United States Patent
Lippard et al.

(10) Patent No.: US 11,203,608 B2
(45) Date of Patent: Dec. 21, 2021

(54) PLATINUM-CONTAINING COMPOUNDS, AND RELATED COMPOSITIONS AND USES THEREOF

(71) Applicant: Massachusetts Institute of Technology, Cambridge, MA (US)

(72) Inventors: Stephen J. Lippard, Washington, DC (US); Omer Yilmaz, Cambridge, MA (US); Fang Wang, Cambridge, MA (US); Jonathan Braverman, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/839,629

(22) Filed: Apr. 3, 2020

(65) Prior Publication Data

US 2020/0331942 A1 Oct. 22, 2020

Related U.S. Application Data

(60) Provisional application No. 62/836,145, filed on Apr. 19, 2019.

(51) Int. Cl.
*C07F 15/00* (2006.01)
*A61P 35/00* (2006.01)

(52) U.S. Cl.
CPC .......... *C07F 15/0093* (2013.01); *A61P 35/00* (2018.01)

(58) Field of Classification Search
None
See application file for complete search history.

(56) References Cited

FOREIGN PATENT DOCUMENTS

WO    WO 2013/103301 A2    7/2013

OTHER PUBLICATIONS

International Search Report and Written Opinion for PCT/US2020/026606 dated Jun. 22, 2020.
(Continued)

*Primary Examiner* — Clinton A Brooks
(74) *Attorney, Agent, or Firm* — Wolf, Greenfield & Sacks, P.C.

(57) ABSTRACT

Platinum-containing compounds are generally described. For example, compounds of Formula (II) are generally described. Inventive compositions and uses thereof are also described. For example, methods of treating cancer in a subject comprising administering to the subject a therapeutically effective amount of a compound of Formula (II) are generally described.

Formula (II)

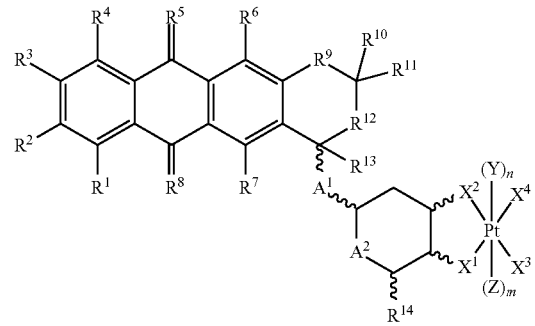

10 Claims, 14 Drawing Sheets

(56) References Cited

OTHER PUBLICATIONS

Alcindor et al., Oxaliplatin: a review in the era of molecularly targeted therapy. Curr Oncol. Jan. 2011;18(1):18-25. doi: 10.3747/co.v18i1.708. PMID: 21331278; PMCID: PMC3031353.
Chien et al., Cellular Mechanisms of Resistance to Anthracyclines and Taxanes in Cancer: Intrinsic and Acquired. Semin. Oncol. 2008, 35, S1-S14.
Chin et al., Ratiometric Delivery of Cisplatin and Doxorubicin using Tumour-Targeting Carbon-Nanotubes Entrapping Platinum(IV) Prodrugs. Chem. Sci. 2014; 5:2265-2270.
Cotterill et al., Chemoenzymatic Synthesis of N-Trifluoroacetyl Doxorubicin-14-Valerate (Valrubicin). Org. Process Res. Dev. 2005, 9, 818-821.
Fu et al., Clinical application of oxaliplatin in epithelial ovarian cancer. Int J Gynecol Cancer. Sep.-Oct. 2006;16(5):1717-32. doi: 10.1111/j.1525-1438.2006.00654.x. PMID: 17009963.
Fuks et al., Structure and biological activity of cationic [PtLCI(DMSO)]NO(3).DMSO complex containing a chelated diaminosugar: methyl-3,4-diamino-2,3,4,6-tetradeoxy-alpha-L-lyxopyranoside. Eur J Med Chem. Jul.-Aug. 2003;38(7-8):775-80. doi: 10.1016/s0223-5234(03)00139-9. PMID: 12932909.
Fulmer et al., NMR Chemical Shifts of Trace Impurities: Common Laboratory Solvents, Organics, and Gases in Deuterated Solvents Relevant to the Organometallic Chemist. Organometallics 2010, 29, 2176-2179.
Gewirtz, A critical evaluation of the mechanisms of action proposed for the antitumor effects of the anthracycline antibiotics adriamycin and daunorubicin. Biochem Pharmacol. Apr. 1, 1999;57(7):727-41. doi: 10.1016/s0006-2952(98)00307-4. PMID: 10075079.
Graham et al., Oxaliplatin. Nat Rev Drug Discov. Jan. 2004;3(1):11-2. doi: 10.1038/nrd1287.PMID: 14756144.
Hortobágyi, Anthracyclines in the treatment of cancer. An overview. Drugs. 1997;54 Suppl 4:1-7. doi: 10.2165/00003495-199700544-00003. PMID: 9361955.
Ikeda et al., Synthesis of 3"-Dehydro-4-O-methylbarminomycin II Having an Eight-membered Acetal-azomethine Ring. Chem. Lett. 1990, 19, 1431-1432.
Johnstone et al., The Next Generation of Platinum Drugs: Targeted Pt(II) Agents, Nanoparticle Delivery, and Pt(IV) Prodrugs. Chem Rev. Mar. 9, 2016;116(5):3436-86. doi: 10.1021/acs.chemrev.5b00597. Epub Feb. 11, 2016. PMID: 26865551; PMCID: PMC4792284.
Johnstone et al., Understanding and improving platinum anticancer drugs—phenanthriplatin. Anticancer Res. Jan. 2014;34(1):471-6. PMID: 24403503; PMCID: PMC3937549.
Kimura et al., Novel Glycosidation of 4-Demethoxyanthracyclinones by the Use of Trimethylsilyl Triflate. Syntheses of Optically Active 4-Demethoxydaunorubicin and 4-Demethoxyadriamycin. Bull. Chem. Soc. Jpn. 1986, 59, 423-431.
Minotti et al., Anthracyclines: molecular advances and pharmacologic developments in antitumor activity and cardiotoxicity. Pharmacol Rev. Jun. 2004;56(2): 185-229. doi: 10.1124/pr.56.2.6. PMID: 15169927.
Monneret, Recent developments in the field of antitumour anthracyclines. Eur J Med Chem. Jun. 2001;36(6):483-93. doi: 10.1016/s0223-5234(01)01244-2. PMID: 11525839.
Musso et al., Perspectives in the development of hybrid bifunctional antitumour agents. Biochem Pharmacol. Aug. 15, 2015;96(4):297-305. doi: 10.1016/j.bcp.2015.06.006. Epub Jun. 11, 2015. PMID: 26074269.
Namikawa et al., Treatment using oxaliplatin and S-1 adjuvant chemotherapy for pathological stage III gastric cancer: a multicenter phase II study (TOSA trial) protocol. BMC Cancer. Feb. 13, 2018;18(1):186. doi: 10.1186/s12885-018-4109-z. PMID: 29439671; PMCID: PMC5812232.
Nitiss, Targeting DNA topoisomerase II in cancer chemotherapy. Nat Rev Cancer. May 2009;9(5):338-50. doi: 10.1038/nrc2607. Epub Apr. 20, 2009. PMID: 19377506; PMCID: PMC2748742.
Pendyala et al., Cytotoxicity, cellular accumulation and DNA binding of oxaliplatin isomers. Cancer Lett. Nov. 6, 1995;97(2):177-84. doi: 10.1016/0304-3835(95)03974-2. PMID: 7497460.
Pommier et al., DNA topoisomerases and their poisoning by anti-cancer and antibacterial drugs. Chem Biol. May 28, 2010;17(5):421-33. doi: 10.1016/j.chembiol.2010.04.012. PMID: 20534341; PMCID: PMC7316379.
Riddell, Cisplatin and Oxaliplatin: Our Current Understanding of Their Actions. Met Ions Life Sci. Feb. 5, 2018;18:/books/9783110470734/9783110470734-007/9783110470734-007.xml. doi: 10.1515/9783110470734-007. PMID: 29394020.
Shen et al., Cisplatin resistance: a cellular self-defense mechanism resulting from multiple epigenetic and genetic changes. Pharmacol Rev. Jul. 2012;64(3):706-21. doi: 10.1124/pr.111.005637. Epub Jun. 1, 2012. PMID: 22659329; PMCID: PMC3400836.
Siddik et al., Antitumor activity of isomeric 1,2-diaminocyclohexane platinum(IV) complexes. J Cancer Res Clin Oncol. 1994;120(7):409-14. doi: 10.1007/BF01240140. PMID: 8188734.
Szakács et al., Targeting multidrug resistance in cancer. Nat Rev Drug Discov. Mar. 2006;5(3):219-34. doi: 10.1038/nrd1984. PMID: 16518375.
Tacar et al., Doxorubicin: an update on anticancer molecular action, toxicity and novel drug delivery systems. J Pharm Pharmacol. Feb. 2013;65(2):157-70. doi: 10.1111/j.2042-7158.2012.01567.x. Epub Aug. 2, 2012. PMID: 23278683.
Trachootham et al., Targeting cancer cells by ROS-mediated mechanisms: a radical therapeutic approach? Nat Rev Drug Discov. Jul. 2009;8(7):579-91. doi: 10.1038/nrd2803. Epub May 29, 2009. PMID: 19478820.
Tsavaris et al., Second-line treatment with oxaliplatin, leucovorin and 5-fluorouracil in gemcitabine-pretreated advanced pancreatic cancer: A phase II study. Invest New Drugs. 2005. Aug. 23(4):369-75. doi: 10.1007/s10637-005-1446-y. Erratum in: Invest New Drugs. Dec. 2005;23(6):603. Kopteridis, Petros [corrected to Kopterides, Petros]. PMID: 16012797.
Umezawa et al., Synthesis of 4-demethoxy-11-deoxy-analogs of daunomycin and adriamycin. J Antibiot (Tokyo). Dec. 1980;33(12):1581-5. doi: 10.7164/antibiotics.33.1581. PMID: 7195898.
Varbanov et al., Oxaliplatin reacts with DMSO only in the presence of water. Dalton Trans. Jul. 18, 2017;46(28):8929-8932. doi: 10.1039/c7dt01628j. PMID: 28654098.
Vásquez-Vivar et al., Endothelial nitric oxide synthase-dependent superoxide generation from adriamycin. Biochemistry. Sep. 23, 1997;36(38):11293-7. doi: 10.1021/bi971475e. PMID: 9333325.
Vollano et al., Comparative antitumor studies on platinum(II) and platinum(IV) complexes containing 1,2-diaminocyclohexane. J Med Chem. Apr. 1987;30(4):716-9. doi: 10.1021/jm00387a023. PMID: 3560163.
Yolles et al., Controlled Release of Biologically Active Agents. ACS Symposium Series. Jun. 1, 1976;33:123-134.
Zhao et al., Enhanced anti-cancer efficacy to cancer cells by doxorubicin loaded water-soluble amino acid-modified β-cyclodextrin platinum complexes. J Inorg Biochem. Aug. 2014;137:31-9. doi: 10.1016/j.jinorgbio.2014.03.012. Epub Apr. 3, 2014. PMID: 24803024.
Zunino et al., Evaluation of a platinum-doxorubicin complex in experimental tumor systems. Invest New Drugs. Nov. 1990;8(4):341-5. doi: 10.1007/BF00198589. PMID: 2084067.
Zunino et al., Synthesis and antitumor activity of a platinum (II)-doxorubicin complex. Cancer Chemother Pharmacol. 1986;18(2):180-2. doi: 10.1007/BF00262293. PMID: 3791563.
Pasini et al., A doxorubicin-Pt(II) complex. Chemistry and antitumor activity. Inorganica Chim Acta. Jul. 1987;137(1-2):123-124.

PLATINUM-CONTAINING COMPOUNDS, AND RELATED COMPOSITIONS AND USES THEREOF

RELATED APPLICATIONS

This application claims the priority benefit under 35 U.S.C. § 119(e) of U.S. Provisional Patent Application Ser. No. 62/836,145, filed Apr. 19, 2019, and entitled "Platinum-Containing Compounds, and Related Compositions and Uses Thereof," which is incorporated herein by reference in its entirety for all purposes.

GOVERNMENT SPONSORSHIP

This invention was made with Government support under Grant Nos. R01 CA211184 and R01 CA034992 awarded by the National Institutes of Health (NIH). The Government has certain rights in the invention.

TECHNICAL FIELD

Platinum-containing compounds, and related compositions and uses thereof, are generally described.

BACKGROUND

Platinum-based agents, such as cisplatin, carboplatin, and oxaliplatin (see, e.g., FIG. 1) are frequently used as anti-cancer agents. The antitumor activity of platinum drugs is mainly attributed to platinum-DNA interactions, which kill cells through DNA synthesis inhibition or transcription inhibition. Despite the high potency of platinum agents, the clinical use of these drugs is limited by inherent and acquired resistance through different cellular self-defense mechanisms, including reduced accumulation of the platinum compounds, increased levels of nucleotide excision repair (NER), and detoxification by glutathione or metallothioneins.

Anthracycline antibiotics (see, e.g., FIG. 2) have been used for the treatment of a broad spectrum of cancers for several decades. The mechanism of the antiproliferative effects of doxorubicin is not fully understood. Two pathways are frequently invoked to account for the anticancer activity of anthracyclines. The first proposal posits that anthracyclines inhibit topoisomerase II (Top2), an enzyme that cleaves and reseals double strands to facilitate DNA replication and transcription. The formation of stable ternary complexes of anthracycline-Top2-DNA leads to DNA double helix breaks by impeding DNA resealing. The second proposed mechanism involves doxorubicin-induced generation of reactive oxygen species (ROS) that results in lipid peroxidation and DNA damage. The redox chemistry of doxorubicin and its ability to chelate intracellular iron, which can trigger a Fenton-type reaction, are suggested as the chemical basis of this process. Anthracyclines are, nevertheless, also hampered by rapidly developed resistance in tumor cells, which is caused by ATP-binding cassette (ABC) transporter-mediated drug efflux.

Thus, new compounds useful in treating diseases, such as cancers, are needed.

SUMMARY

Platinum-containing compounds are generally described, as well as compositions, methods, and uses thereof. For example, in some embodiments, the platinum-containing compound comprises a moiety that comprises a portion of an anthracycline drug (e.g., a moiety that comprises a portion of doxorubicin) conjugated to a platinum-containing moiety. In certain embodiments, the compounds disclosed herein, and related compositions thereof, can be used for treating a disease in a subject in need thereof. For example, in some cases, the compounds disclosed herein, and related compositions thereof, can be used for treating a proliferative disease (e.g., cancer, such as ovarian cancer, colorectal cancer, breast cancer, lung cancer, prostate cancer, osteosarcoma, and/or leukemia, inflammatory diseases, or autoimmune diseases) in a subject in need thereof. The subject matter of the present invention involves, in some cases, interrelated products, alternative solutions to a particular problem, and/or a plurality of different uses of one or more systems and/or articles.

Certain embodiments are related to platinum-containing compounds, or compositions thereof.

In some embodiments, the compound is a compound of Formula (I):

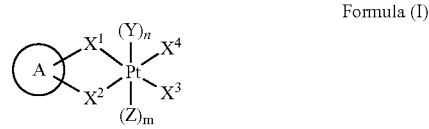

Formula (I)

or a pharmaceutically acceptable salt, solvate, hydrate, polymorph, co-crystal, tautomer, stereoisomer, isotopically labeled derivative, or prodrug thereof;

wherein A comprises at least 70% of the structure of an anthracycline drug;

wherein $X^1$ and $X^2$ are each independently selected from the group consisting of amino, alkylamino, arylamino, dialkylamino, diarylamino, oxygen, hydroxy, alkoxy, aryloxy, siloxy, sulfur, thiol, alkyl sulfide, aryl sulfide, alkyl sulfoxide, aryl sulfoxide, sulfinate, selenium, selenol, alkyl selenide, aryl selenide, alkyl selenoxide, aryl selenoxide, and seleninate;

wherein $X^3$ and $X^4$ are each independently selected from the group consisting of amino, alkylamino, arylamino, dialkylamino, diarylamino, heteroarylene, water, halide, carboxylate, hydroxide, alkoxide, aryloxide, siloxide, dialkyl sulfide, diaryl sulfide, alkyl aryl sulfide, dialkyl sulfoxide, diaryl sulfoxide, alkyl aryl sulfoxide, alkyl sulfinate, aryl sulfinate, alkyl sulfonate, aryl sulfonate, sulfite, sulfate, thiosulfate, dialkyl selenide, diaryl selenide, alkyl aryl selenide, dialkyl selenoxide, diaryl selenoxide, alkyl aryl selenoxide, selenite, and seleninate;

wherein Y and Z are each independently selected from the group consisting of hydroxide, alkoxide, aryloxide, siloxide, and halide;

wherein n is 0 or 1;

wherein m is 0 or 1; and wherein A, Y, Z, $X^1$, $X^2$, $X^3$, and/or $X^4$ are each independently optionally substituted.

In certain embodiments, the compound is a compound of Formula (II) and/or the composition comprises a compound of Formula (II):

Formula (II)

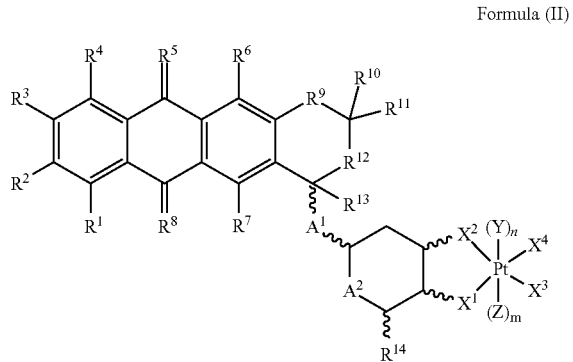

or a pharmaceutically acceptable salt, solvate, hydrate, polymorph, co-crystal, tautomer, stereoisomer, isotopically labeled derivative, or prodrug thereof;

wherein $R^1$, $R^2$, $R^3$, $R^4$, $R^6$, and $R^7$ are each independently selected from the group consisting of hydrogen, alkyl, aryl, halogen, oxygen, hydroxy, alkoxy, aryloxy, siloxy, amino, alkylamino, arylamino, dialkylamino, diarylamino, imine, alkylimine, arylimine, and —OM;

wherein M is a cation;

wherein $R^5$ and $R^8$ are each independently selected from the group consisting of hydrogen, alkyl, aryl, halogen, oxygen, hydroxy, alkoxy, aryloxy, siloxy, amino, alkylamino, arylamino, dialkylamino, diarylamino, imine, alkylimine, arylimine, and —OM;

wherein $R^9$ and $R^{12}$ are each independently selected from the group consisting of —CR(R')—, carbonyl, imine, alkylimine, and arylimine;

wherein R and R' are independently selected from the group consisting of hydrogen, alkyl, aryl, halogen, hydroxy, alkoxy, aryloxy, siloxy, amino, alkylamino, arylamino, dialkylamino, and diarylamino;

wherein $R^{10}$ and $R^{11}$ are each independently selected from the group consisting of hydrogen, halogen, hydroxy, alkoxy, aryloxy, siloxy, amino, alkylamino, arylamino, dialkylamino, diarylamino, —(C=O)—(CH$_2$)$_k$R$^{15}$, —(CHOR$^{16}$)—(CH$_2$)$_k$R$^{15}$, —(C=NR$^{16}$)—(CH$_2$)$_k$R$^{15}$, —(CHNHR$^{16}$)—(CH$_2$)$_k$R$^{15}$, and —(CHNR$^{16}$$_2$)—(CH$_2$)$_k$R$^{15}$;

wherein $R^{15}$ is selected from the group consisting of hydrogen, halogen, hydroxy, alkoxy, aryloxy, and siloxy;

wherein $R^{16}$ is selected from the group consisting of hydrogen, alkyl, aryl, and silyl;

wherein k is 0, 1, 2, or 3;

wherein $R^{13}$ and $R^{14}$ are each independently selected from the group consisting of hydrogen, halogen, alkyl, and aryl;

wherein $A^1$ and $A^2$ are each independently selected from the group consisting of oxygen, sulfur, and —NR$^{17}$—;

wherein $R^{17}$ is selected from the group consisting of hydrogen, alkyl, and aryl;

wherein $X^1$ and $X^2$ are each independently selected from the group consisting of amino, alkylamino, arylamino, dialkylamino, diarylamino, oxygen, hydroxy, alkoxy, aryloxy, siloxy, sulfur, thiol, alkyl sulfide, aryl sulfide, alkyl sulfoxide, aryl sulfoxide, sulfinate, selenium, selenol, alkyl selenide, aryl selenide, alkyl selenoxide, aryl selenoxide, and seleninate;

wherein $X^3$ and $X^4$ are each independently selected from the group consisting of amino, alkylamino, arylamino, dialkylamino, diarylamino, heteroarylene, water, halide, carboxylate, hydroxide, alkoxide, aryloxide, siloxide, dialkyl sulfide, diaryl sulfide, alkyl aryl sulfide, dialkyl sulfoxide, diaryl sulfoxide, alkyl aryl sulfoxide, alkyl sulfinate, aryl sulfinate, alkyl sulfonate, aryl sulfonate, sulfite, sulfate, thiosulfate, dialkyl selenide, diaryl selenide, alkyl aryl selenide, dialkyl selenoxide, diaryl selenoxide, alkyl aryl selenoxide, selenite, and seleninate;

wherein Y and Z are each independently selected from the group consisting of hydroxide, alkoxide, aryloxide, siloxide, and halide;

wherein n is 0 or 1;

wherein m is 0 or 1; and wherein M, Y, Z, $A^1$, $A^2$, $X_1$, $X^2$, $X^3$, $X^4$, R, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ are each independently optionally substituted.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

DETAILED DESCRIPTION

Figure 1:
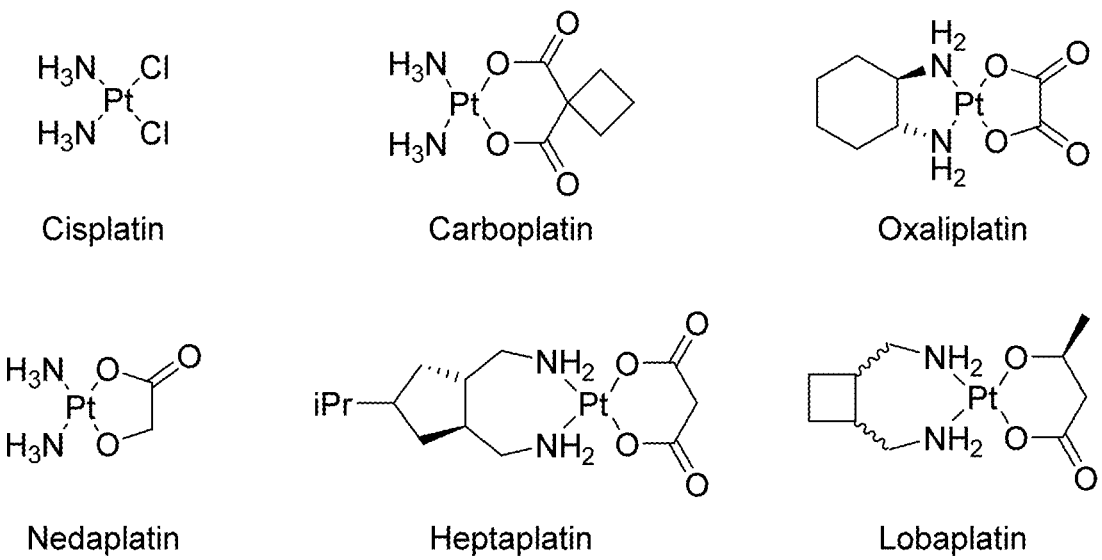
FIG. 1 shows the chemical structures of clinically approved platinum agents for cancer treatment.
Figure 2:
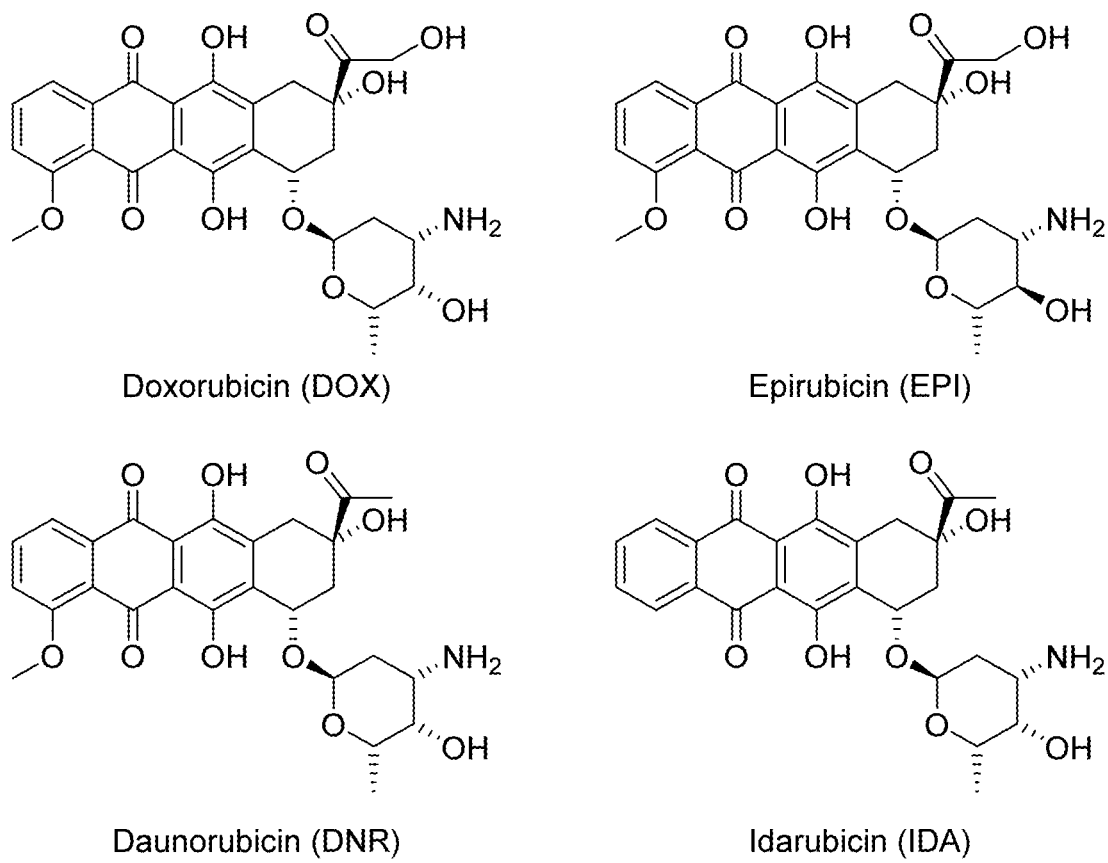
FIG. 2 shows the chemical structures of some anthracyclines used clinically.

Compounds, compositions thereof, preparative methods thereof, and related therapeutic methods are disclosed herein. For example, disclosed herein are platinum-containing compounds, and compositions and uses thereof. In some embodiments, the platinum-containing compound comprises a moiety that comprises a portion of an anthracycline drug (e.g., a moiety that comprises a portion of doxorubicin) conjugated to a platinum-containing moiety. In certain embodiments, the compounds disclosed herein, and related compositions thereof, can be used for treating a disease in a subject in need thereof. For example, in some cases, the compounds disclosed herein, and related compositions thereof, can be used for treating cancer (e.g., ovarian cancer, colorectal cancer, breast cancer, lung cancer, prostate cancer, osteosarcoma, and/or leukemia), as well as other diseases caused by abnormal cell proliferation and growth in a subject in need thereof.

As discussed above, there is increasing resistance to platinum-based agents and to anthracycline drugs. The in vivo efficacy of two agents (e.g., a platinum-based agent and an anthracycline drug) when merely combined is frequently significantly attenuated. This attenuation can be due, in part, to the different pharmacokinetics and tissue distributions of each drug, which can lead to difficulty in delivering them to the target at the respective optimal concentrations. However, it was unexpectedly discovered that, in some embodiments, the chemical conjugation of platinum-based agents to anthracyclines through non-labile covalent bonds modulates the activity and toxicity profile of both agents. In some embodiments, the two therapeutically active components are able to reach their destination molecular target together in cancer cells and simultaneously exert their cytotoxic activities. Thus, it was unexpectedly discovered that the product of covalently conjugating two pharmacophores might, in certain embodiments, be superior to the simple physical combination of the same two agents. In certain embodiments, a platinum-anthracycline conjugate might exhibit additional beneficial anticancer properties. For example, in some cases, the conjugate might act against cancer cells by the mechanisms of both the platinum agent and the anthracycline, thereby increasing its potency relative to either drug alone. In certain instances, cells resistant to the platinum agent, the anthracycline, or both might still be sensitive to the platinum-anthracycline conjugate. Additional details regarding the platinum-containing compounds, and compositions and uses thereof, are provided below.

Certain aspects are related to platinum-containing compounds.

In some embodiments, the compound is a compound of Formula (I):

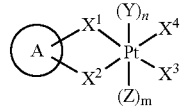

Formula (I)

or a pharmaceutically acceptable salt, solvate, hydrate, polymorph, co-crystal, tautomer, stereoisomer, isotopically labeled derivative, or prodrug thereof;

wherein $X^1$ and $X^2$ are each independently selected from the group consisting of amino, alkylamino, arylamino, dialkylamino, diarylamino, oxygen hydroxy, alkoxy, aryloxy, siloxy, sulfur, thiol, alkyl sulfide, aryl sulfide, alkyl sulfoxide, aryl sulfoxide, sulfinate, selenium, selenol, alkyl selenide, aryl selenide, alkyl selenoxide, aryl selenoxide, and seleninate;

wherein $X^3$ and $X^4$ are each independently selected from the group consisting of amino, alkylamino, arylamino, dialkylamino, diarylamino, heteroarylene, water, halide, carboxylate, hydroxide, alkoxide, aryloxide, siloxide, dialkyl sulfide, diaryl sulfide, alkyl aryl sulfide, dialkyl sulfoxide, diaryl sulfoxide, alkyl aryl sulfoxide, alkyl sulfinate, aryl sulfinate, alkyl sulfonate, aryl sulfonate, sulfite, sulfate, thiosulfate, dialkyl selenide, diaryl selenide, alkyl aryl selenide, dialkyl selenoxide, diaryl selenoxide, alkyl aryl selenoxide, selenite, and seleninate;

wherein Y and Z are each independently selected from the group consisting of hydroxide, alkoxide, aryloxide, siloxide, and halide;

wherein n is 0 or 1;

wherein m is 0 or 1; and wherein A, Y, Z, $X^1$, $X^2$, $X^3$, and/or $X^4$ are each independently optionally substituted.

In certain embodiments, A comprises at least 70%, at least 80%, at least 90%, at least 95%, or at least 99% of the structure of an anthracycline drug. In some instances, A comprises less than or equal to 100%, less than or equal to 99%, less than or equal to 95%, less than or equal to 90%, or less than or equal to 80% of the structure of an anthracycline drug. Combinations of these ranges are also possible (e.g., 90-95% of the structure of an anthracycline drug).

The percentage of the anthracycline drug included in A is calculated by determining the percentage of the molecular weight of the portions of the anthracycline drug included in A versus the molecular weight of the anthracycline drug. For example, if the compound comprises doxaliplatin—a compound of Formula (I)—(shown below on the left), wherein A is the portion of doxaliplatin that is not in the box, and wherein A differs from doxorubicin (shown below on the right) only in that the boxed portion of doxorubicin is not included in A (because the two amino groups in the box shown in doxaliplatin are $X^1$ and $X^2$ of Formula (I) rather than part of A), A comprises 93.92% of the structure of an anthracycline drug (doxorubicin):

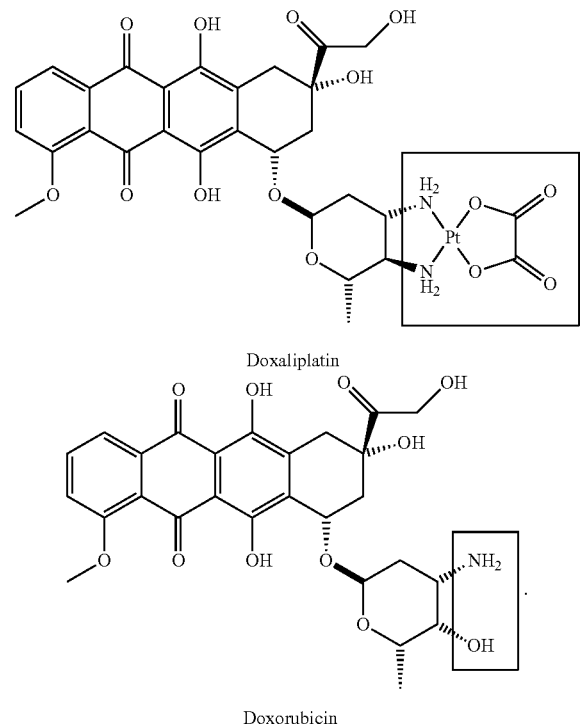

Doxaliplatin

Doxorubicin

If the molecular weight of doxorubicin is 543.52 g/mol, and A includes all of doxorubicin except an $NH_2$ group and an OH group, which have molecular weights of 16.02 g/mol and 17.00 g/mol, respectively, then A comprises 93.92% ((543.52-16.02-17.00)/543.52×100) of the anthracycline drug.

In accordance with some embodiments, the portion of the anthracycline drug included in A is at least 70%, at least 80%, at least 90%, at least 95%, or at least 99% of A. In certain embodiments, the portion of the anthracycline drug included in A is less than or equal to 100%, less than or equal to 99%, less than or equal to 95%, less than or equal to 90%, or less than or equal to 80% of A. Combinations of these ranges are also possible (e.g., 90-99% of A is the portion of the anthracycline drug).

The percentage of A that is the portion of the anthracycline drug is calculated by determining the percentage of the molecular weight of the portion of the anthracycline drug versus the total molecular weight of A. In the example discussed above, the molecular weight of the portion of the anthracycline drug (doxorubicin) included in A was 510.5 g/mol (543.52-16.02-17.00), and the total molecular weight of A was 510.5 g/mol; thus, in this example, the portion of the anthracycline drug included in A is 100% of A.

In some embodiments, the anthracycline drug is FDA-approved. In certain embodiments, the anthracycline drug is not FDA-approved. In some cases, the anthracycline drug is selected from the group consisting of doxorubicin, epirubicin, daunorubicin, idarubicin, and valrubicin. For example, in certain instances, the anthracycline drug is doxorubicin.

In some instances, $X^1$ and/or $X^2$ are an amino group. For example, in doxaliplatin, both $X^1$ and $X^2$ are $NH_2$.

In certain embodiments, $X^3$ and/or $X^4$ is a halide. In accordance with some embodiments, $X^3$ and/or $X^4$ is a carboxylate. For example, in doxaliplatin, both $X^3$ and $X^4$ are a carboxylate. $X^3$ and $X^4$ are joined together to form a bidentate ligand, in certain cases. For example, in doxaliplatin, $X^3$ and $X^4$ are joined together to form a bidentate ligand. According to some embodiments, $X^3$ and $X^4$ can be joined with one of $X^1$ and $X^2$ to form a tridentate ligand. Still further, in certain embodiments, both $X^3$ and $X^4$ can be joined with $X^1$ and $X^2$ to form a tetradentate ligand.

In some cases, n and m are both 1. In other cases, n and m are both 0. For example, in doxaliplatin, n and m are both 0.

In some embodiments, the compound is a compound of Formula (II):

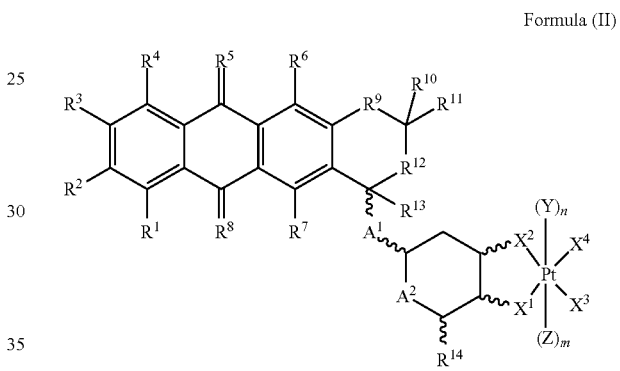

Formula (II)

or a pharmaceutically acceptable salt, solvate, hydrate, polymorph, co-crystal, tautomer, stereoisomer, isotopically labeled derivative, or prodrug thereof;

wherein $R^1$, $R^2$, $R^3$, $R^4$, $R^6$, and $R^7$ are each independently selected from the group consisting of hydrogen, alkyl, aryl, halogen, oxygen, hydroxy, alkoxy, aryloxy, siloxy, amino, alkylamino, arylamino, dialkylamino, diarylamino, imine, alkylimine, arylimine, and —OM;

wherein M is a cation;

wherein $R^5$ and $R^8$ are each independently selected from the group consisting of hydrogen, alkyl, aryl, halogen, oxygen, hydroxy, alkoxy, aryloxy, siloxy, amino, alkylamino, arylamino, dialkylamino, diarylamino, imine, alkylimine, arylimine, and —OM;

wherein $R^9$ and $R^{12}$ are each independently selected from the group consisting of —CR(R')—, carbonyl, imine, alkylimine, and arylimine;

wherein R and R' are independently selected from the group consisting of hydrogen, alkyl, aryl, halogen, hydroxy, alkoxy, aryloxy, siloxy, amino, alkylamino, arylamino, dialkylamino, and diarylamino;

wherein $R^{10}$ and $R^{11}$ are each independently selected from the group consisting of hydrogen, halogen, hydroxy, alkoxy, aryloxy, siloxy, amino, alkylamino, arylamino, dialkylamino, diarylamino, —(C═O)—$(CH_2)_k R^{15}$, —(CH-O$R^{16}$)—$(CH_2)_k R^{15}$, —(C═N$R^{16}$)—$(CH_2)_k R^{15}$, —(CHN-H$R^{16}$)—$(CH_2)_k R^{15}$, and —(CHN$R^{16}_2$)—$(CH_2)_k R^{15}$;

wherein $R^{15}$ is selected from the group consisting of hydrogen, halogen, hydroxy, alkoxy, aryloxy, and siloxy;

wherein R$^{16}$ is selected from the group consisting of hydrogen, alkyl, aryl, and silyl;

wherein k is 0, 1, 2, or 3;

wherein R$^{13}$ and R$^{14}$ are each independently selected from the group consisting of hydrogen, halogen, alkyl, and aryl;

wherein A$^1$ and A$^2$ are each independently selected from the group consisting of oxygen, sulfur, and —NR$^{17}$;

wherein R$^{17}$ is selected from the group consisting of hydrogen, alkyl, and aryl;

wherein X$^1$ and X$^2$ are each independently selected from the group consisting of amino, alkylamino, arylamino, dialkylamino, diarylamino, oxygen, hydroxy, alkoxy, aryloxy, siloxy, sulfur, thiol, alkyl sulfide, aryl sulfide, alkyl sulfoxide, aryl sulfoxide, sulfinate, selenium, selenol, alkyl selenide, aryl selenide, alkyl selenoxide, aryl selenoxide, and seleninate; wherein X$^3$ and X$^4$ are each independently selected from the group consisting of amino, alkylamino, arylamino, dialkylamino, diarylamino, heteroarylene, water, halide, carboxylate, hydroxide, alkoxide, aryloxide, siloxide, dialkyl sulfide, diaryl sulfide, alkyl aryl sulfide, dialkyl sulfoxide, diaryl sulfoxide, alkyl aryl sulfoxide, alkyl sulfinate, aryl sulfinate, alkyl sulfonate, aryl sulfonate, sulfite, sulfate, thiosulfate, dialkyl selenide, diaryl selenide, alkyl aryl selenide, dialkyl selenoxide, diaryl selenoxide, alkyl aryl selenoxide, selenite, and seleninate; wherein Y and Z are each independently selected from the group consisting of hydroxide, alkoxide, aryloxide, siloxide, and halide;

wherein n is 0 or 1;

wherein m is 0 or 1; and wherein M, Y, Z, A$^1$, A$^2$, X$^1$, X$^2$, X$^3$, X$^4$, R, R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, and/or R$^{17}$ are each independently optionally substituted.

As used herein, a wavy bond indicates that the stereochemistry is unspecified, and encompasses all possible stereochemistries.

In some instances, X$^1$ and/or X$^2$ are amino. For example, in doxaliplatin, both X$^1$ and X$^2$ are NH$_2$. In some cases, X$^1$ and X$^2$ are joined together to form a bidentate ligand.

In certain embodiments, X$^3$ and/or X$^4$ is a halide. In accordance with some embodiments, X$^3$ and/or X$^4$ is a carboxylate. For example, in doxaliplatin, both X$^3$ and X$^4$ are a carboxylate. X$^3$ and X$^4$ are joined together to form a bidentate ligand, in certain cases. For example, in doxaliplatin, X$^3$ and X$^4$ are joined together to form a bidentate ligand. According to some embodiments, X$^3$ and X$^4$ can be joined with one of X$^1$ and X$^2$ to form a tridentate ligand. Still further, in certain embodiments, both X$^3$ and X$^4$ can be joined with X$^1$ and X$^2$ to form a tetradentate ligand.

In some cases, n and m are both 1. In other cases, n and m are both 0. For example, in doxaliplatin, n and m are both 0.

In certain embodiments, M is selected from the group consisting of ammonium, tetra-alkyl ammonium, trialkylphenyl ammonium, lithium, sodium, potassium, magnesium, calcium, zinc, cobalt, copper, and iron.

According to some embodiments, R$^2$, R$^3$, R$^4$, and/or R$^{13}$ are hydrogen.

In accordance with certain embodiments, R$^6$, R$^7$, and/or R$^{10}$ are hydroxy.

In some cases, R$^9$ and/or R$^{12}$ are methylene.

A$^1$, A$^2$, R$^5$, and/or R$^8$ are oxygen, in some instances.

R$^1$, in certain cases, is alkoxy.

In some embodiments, R$^{11}$ is —(C═O)—(CH$_2$)$_k$R$^{15}$. R$^{15}$ is hydroxy, in some cases.

In certain instances, k is 1.

According to certain embodiments, R$^2$, R$^3$, R$^4$, and/or R$^{13}$ are hydrogen; A$^1$, A$^2$, R$^5$, and/or R$^8$ are oxygen; R$^1$ is alkoxy; R$^{11}$ is —(C═O)—(CH$_2$)$_k$R$^{15}$; R$^{15}$ is hydroxy; and/or k is 1.

In some embodiments, the compound of Formula (I) or Formula (II) is:

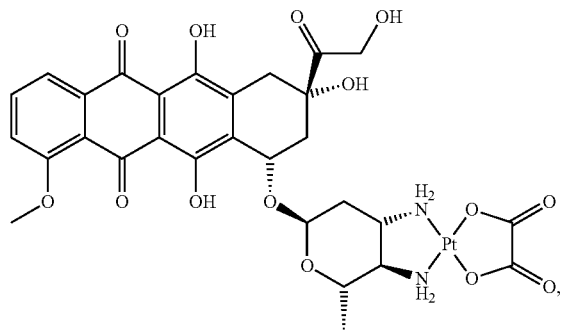

or a pharmaceutically acceptable salt, solvate, hydrate, polymorph, co-crystal, tautomer, stereoisomer, isotopically labeled derivative, or prodrug thereof.

In certain embodiments, the compound of Formula (I) or Formula (II) is:

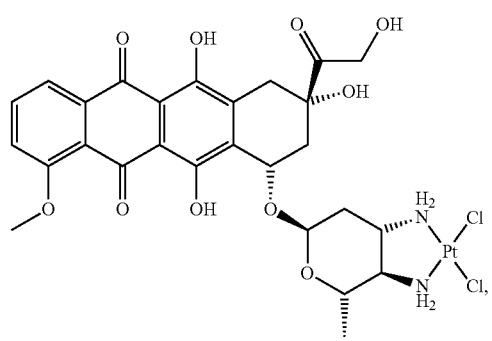

or a pharmaceutically acceptable salt, solvate, hydrate, polymorph, co-crystal, tautomer, stereoisomer, isotopically labeled derivative, or prodrug thereof.

According to some embodiments, the compound of Formula (I) or Formula (II) is:

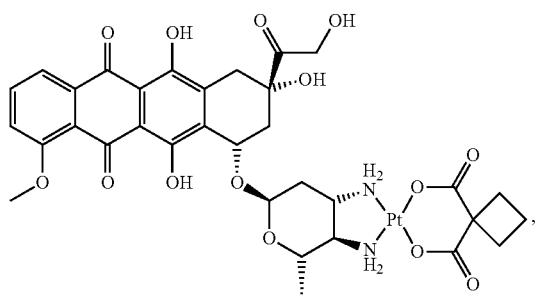

or a pharmaceutically acceptable salt, solvate, hydrate, polymorph, co-crystal, tautomer, stereoisomer, isotopically labeled derivative, or prodrug thereof.

In some embodiments, the compound is a compound of Formula (III):

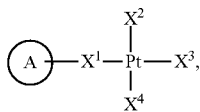

Formula (III)

or a pharmaceutically acceptable salt, solvate, hydrate, polymorph, co-crystal, tautomer, stereoisomer, isotopically labeled derivative, or prodrug thereof;

wherein A comprises at least 70% of the structure of an anthracycline drug;

wherein $X^1$ is selected from the group consisting of amino, alkylamino, arylamino, dialkylamino, and diarylamino;

wherein $X^2$, $X^3$, and $X^4$ are each independently selected from the group consisting of amino, alkylamino, arylamino, dialkylamino, diarylamino, heteroarylene, water, halide, carboxylate, hydroxide, alkoxide, aryloxide, siloxide, dialkyl sulfide, diaryl sulfide, alkyl aryl sulfide, dialkyl sulfoxide, diaryl sulfoxide, alkyl aryl sulfoxide, alkyl sulfinate, aryl sulfinate, alkyl sulfonate, aryl sulfonate, sulfite, sulfate, thiosulfate, dialkyl selenide, diaryl selenide, alkyl aryl selenide, dialkyl selenoxide, diaryl selenoxide, alkyl aryl selenoxide, selenite, and seleninate; and wherein A, $X^1$, $X^2$, $X^3$, and/or $X^4$ are each independently optionally substituted.

In certain embodiments, embodiments relating to A, $X^1$, $X^2$, $X^3$, and/or $X^4$ described for Formula (I) apply to Formula (III).

In accordance with some embodiments, the compound is a compound of Formula (IV):

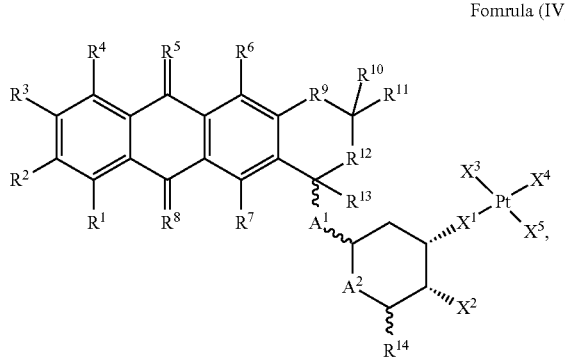

Formula (IV)

or a pharmaceutically acceptable salt, solvate, hydrate, polymorph, co-crystal, tautomer, stereoisomer, isotopically labeled derivative, or prodrug thereof;

wherein $R^1$, $R^2$, $R^3$, $R^4$, $R^6$, and $R^7$ are each independently selected from the group consisting of hydrogen, alkyl, aryl, halogen, oxygen, hydroxy, alkoxy, aryloxy, siloxy, amino, alkylamino, arylamino, dialkylamino, diarylamino, imine, alkylimine, arylimine, and —OM;

wherein M is a cation;

wherein $R^5$ and $R^8$ are each independently selected from the group consisting of hydrogen, alkyl, aryl, halogen, oxygen, hydroxy, alkoxy, aryloxy, siloxy, amino, alkylamino, arylamino, dialkylamino, diarylamino, imine, alkylimine, arylimine, and —OM;

wherein $R^9$ and $R^{12}$ are each independently selected from the group consisting of —CR(R')—. carbonyl, imine, alkylimine, and arylimine;

wherein R and R' are independently selected from the group consisting of hydrogen, alkyl, aryl, halogen, hydroxy, alkoxy, aryloxy, siloxy, amino, alkylamino, arylamino, dialkylamino, and diarylamino;

wherein $R^{10}$ and $R^{11}$ are each independently selected from the group consisting of hydrogen, halogen, hydroxy, alkoxy, aryloxy, siloxy, amino, alkylamino, arylamino, dialkylamino, diarylamino, —(C=O)—(CH$_2$)$_k$R$^{15}$, —(CHOR$^{16}$)—(CH$_2$)$_k$R$^{15}$, —(C=NR$^{16}$)—(CH$_2$)$_k$R$^{15}$, —(CHNHR$^{16}$)—(CH$_2$)$_k$R$^{15}$, and —(CHNR$^{16}{}_2$)—(CH$_2$)$_k$R$^{15}$;

wherein $R^{15}$ is selected from the group consisting of hydrogen, halogen, hydroxy, alkoxy, aryloxy, and siloxy;

wherein $R^{16}$ is selected from the group consisting of hydrogen, alkyl, aryl, and silyl;

wherein k is 0, 1, 2, or 3;

wherein $R^{13}$ and $R^{14}$ are each independently selected from the group consisting of hydrogen, halogen, alkyl, and aryl;

wherein $A^1$ and $A^2$ are each independently selected from the group consisting of oxygen, sulfur, and —NR$^{17}$;

wherein $R^{17}$ is selected from the group consisting of hydrogen, alkyl, and aryl;

wherein $X^1$ is selected from the group consisting of amino, alkylamino, arylamino, dialkylamino, diarylamino;

wherein $X^2$ is selected from the group consisting of hydrogen, halogen, hydroxy, alkoxy, aryloxy, siloxy, alkyl, aryl, azido, and amide;

wherein $X^3$, $X^4$, and $X^5$ are each independently selected from the group consisting of amino, alkylamino, arylamino, dialkylamino, diarylamino, heteroarylene, water, halide, carboxylate, hydroxide, alkoxide, siloxide, dialkyl sulfide, diaryl sulfide, alkyl aryl sulfide, dialkyl sulfoxide, diaryl sulfoxide, alkyl aryl sulfoxide, alkyl sulfinate, aryl sulfinate, alkyl sulfonate, aryl sulfonate, sulfite, sulfate, thiosulfate, dialkyl selenide, diaryl selenide, alkyl aryl selenide, dialkyl selenoxide, diaryl selenoxide, alkyl aryl selenoxide, selenite, and seleninate; and wherein M, $A^1$, $A^2$, $X^1$, $X^2$, $X^3$, $X^4$, $X^5$, R, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and/or $R^{17}$ are each independently optionally substituted.

In certain embodiments, M is selected from the group consisting of ammonium, tetra-alkyl ammonium, trialkylphenyl ammonium, lithium, sodium, potassium, magnesium, calcium, zinc, cobalt, copper, and iron.

In some cases, any combination of two of $X^3$, $X^4$, and $X^5$ can be joined together to form a bidentate ligand.

In certain instances, $X^3$, $X^4$, and $X^5$ can be joined together to form a tridentate ligand.

In certain cases, any of $X^3$, $X^4$, and $X^5$ can be joined with $X^1$ to form a bidentate, ligand.

In some embodiments, any combination of two of $X^3$, $X^4$, and $X^5$ can be joined with $X^1$ to form a tridentate ligand.

In certain embodiments, $X^3$, $X^4$, and $X^5$ can be joined with $X^1$ to form a tetradentate ligand.

In certain embodiments, embodiments relating to M, $A^1$, $A^2$, $X^1$, $X^2$, $X^3$, $X^4$, $X^5$, R, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and/or $R^{17}$ described for Formula (II) apply to Formula (IV).

In accordance with some embodiments, the compound is a compound of Formula (V):

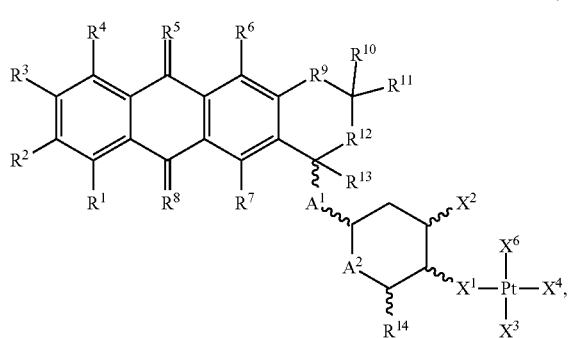

Formula (V)

or a pharmaceutically acceptable salt, solvate, hydrate, polymorph, co-crystal, tautomer, stereoisomer, isotopically labeled derivative, or prodrug thereof;

wherein $R^1$, $R^2$, $R^3$, $R^4$, $R^6$, and $R^7$ are each independently selected from the group consisting of hydrogen, alkyl, aryl, halogen, oxygen, hydroxy, alkoxy, aryloxy, siloxy, amino, alkylamino, arylamino, dialkylamino, diarylamino, imine, alkylimine, arylimine, and —OM;

wherein M is a cation;

wherein $R^5$ and $R^8$ are each independently selected from the group consisting of hydrogen, alkyl, aryl, halogen, oxygen, hydroxy, alkoxy, aryloxy, siloxy, amino, alkylamino, arylamino, dialkylamino, diarylamino, imine, alkylimine, arylimine, and —OM;

wherein $R^9$ and $R^{12}$ are each independently selected from the group consisting of —CR(R')—, carbonyl, imine, alkylimine, and arylimine;

wherein R and R' are independently selected from the group consisting of hydrogen, alkyl, aryl, halogen, hydroxy, alkoxy, aryloxy, siloxy, amino, alkylamino, arylamino, dialkylamino, and diarylamino;

wherein $R^{10}$ and $R^{11}$ are each independently selected from the group consisting of hydrogen, halogen, hydroxy, alkoxy, aryloxy, siloxy, amino, alkylamino, arylamino, dialkylamino, diarylamino, —(C=O)—$(CH_2)_k R^{15}$, —(CH-$OR^{16}$)—$(CH_2)_k R^{15}$, —(C=$NR^{16}$)—$(CH_2)_k R^{15}$, —(CHN-$HR^{16}$)—$(CH_2)_k R^{15}$, and —(CHN$R^{16}{}_2$)—$(CH_2)_k R^{15}$;

wherein $R^{15}$ is selected from the group consisting of hydrogen, halogen, hydroxy, alkoxy, aryloxy, and siloxy;

wherein $R^{16}$ is selected from the group consisting of hydrogen, alkyl, aryl, and silyl;

wherein k is 0, 1, 2, or 3;

wherein $R^{13}$ and $R^{14}$ are each independently selected from the group consisting of hydrogen, halogen, alkyl, and aryl;

wherein $A^1$ and $A^2$ are each independently selected from the group consisting of oxygen, sulfur, and —$NR^{17}$;

wherein $R^{17}$ is selected from the group consisting of hydrogen, alkyl, and aryl;

wherein $X^1$ is selected from the group consisting of amino, alkylamino, arylamino, dialkylamino, diarylamino, and heteroarylene;

wherein $X^2$ is selected from the group consisting of hydrogen, halogen, hydroxy, alkoxy, aryloxy, siloxy, alkyl, aryl, azido, and amide;

wherein $X^3$, $X^4$, and $X^5$ are each independently selected from the group consisting of amino, alkylamino, arylamino, dialkylamino, diarylamino, heteroarylene, water, halide, carboxylate, hydroxide, alkoxide, aryloxide, siloxide, dialkyl sulfide, diaryl sulfide, alkyl aryl sulfide, dialkyl sulfoxide, diaryl sulfoxide, alkyl aryl sulfoxide, alkyl sulfinate, aryl sulfinate, alkyl sulfonate, aryl sulfonate, sulfite, sulfate, thiosulfate, dialkyl selenide, diaryl selenide, alkyl aryl selenide, dialkyl selenoxide, diaryl selenoxide, alkyl aryl selenoxide, selenite, and seleninate; and wherein M, $A^1$, $A^2$, $X^1$, $X^2$, $X^3$, $X^4$, $X^5$, R, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and/or $R^{17}$ are each independently optionally substituted.

In some cases, any combination of two of $X^3$, $X^4$, and $X^5$ can be joined together to form a bidentate ligand.

In certain embodiments, M is selected from the group consisting of ammonium, tetra-alkyl ammonium, trialkylphenyl ammonium, lithium, sodium, potassium, magnesium, calcium, zinc, cobalt, copper, and iron.

In certain instances, $X^3$, $X^4$, and $X^5$ can be joined together to form a tridentate ligand.

In certain cases, any of $X^3$, $X^4$, and $X^5$ can be joined with $X^1$ to form a bidentate, ligand.

In some embodiments, any combination of two of $X^3$, $X^4$, and $X^5$ can be joined with $X^1$ to form a tridentate ligand.

In certain embodiments, $X^3$, $X^4$, and $X^5$ can be joined with $X^1$ to form a tetradentate ligand.

In certain embodiments, embodiments relating to M, $A^1$, $A^2$, $X^1$, $X^2$, $X^3$, $X^4$, R, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and/or $R^{17}$ described for Formula (II) apply to Formula (V).

According to some embodiments, the compound is a compound of Formulas (I)-(V) or a pharmaceutically acceptable salt thereof.

Certain aspects relate to compositions. As used herein, a composition comprises an active compound (e.g., a platinum-containing compound disclosed herein) and an excipient (e.g., a pharmaceutically acceptable excipient). Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

In certain embodiments, the composition comprises a compound of Formulas (I)-(V) or a pharmaceutically acceptable salt, solvate, hydrate, polymorph, co-crystal, tautomer, stereoisomer, isotopically labeled derivative, or prodrug thereof. In some cases, the composition comprises a compound of Formulas (I)-(V) or a pharmaceutically acceptable salt thereof. In some instances, the composition further comprises a pharmaceutically acceptable excipient.

In some embodiments of Formulas (I)-(V), $X^1$, $X^2$, $X^3$, $X^4$, and/or $X^5$ may dissociate from the platinum center under suitable in vivo conditions.

Certain aspects relate to methods of treating a disease in a subject in need thereof.

In some embodiments, the method comprises administering to the subject a therapeutically effective amount of a compound and/or composition disclosed herein.

According to some embodiments, administering can be accomplished by implanting, absorbing, ingesting, injecting, or inhaling the compound and/or composition.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In some embodiments, a therapeutically effective amount refers to an amount sufficient to treat a disease.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

In certain embodiments, the disease is a proliferative disease. Examples of proliferative diseases include cancer, inflammatory diseases, or autoimmune diseases. Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, women's gynecological cancers, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), blood cancers, hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g, mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.ka. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer, cervical cancer, breast cancer, testicular cancer, lung cancer, and vulvar cancer (e.g., Paget's disease of the vulva). For example, in some embodiments, the cancer is ovarian cancer and/or colorectal cancer.

Examples of possible subjects include, but are not limited to, humans (i.e., a male or female human of any age group, e.g., a pediatric subject (e.g, infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cats, and/or dogs. In certain embodiments, the animal is a mammal. The animal may be a male or female and at any stage of development. A non-human animal may be a transgenic animal.

In accordance with some embodiments, compounds and/or compositions disclosed herein have numerous applications and benefits. For example, in some cases, the compounds and/or compositions disclosed herein are more potent than other drugs. In certain instances, compounds and/or compositions disclosed herein can be used to treat diseases which are resistant to other drugs. In certain embodiments, cells uptake a higher amount of compounds and/or compositions disclosed herein compared to other drugs.

The following examples are intended to illustrate certain embodiments of the present invention, but do not exemplify the full scope of the invention.

Example 1

Oxaliplatin is an FDA-approved platinum agent used for cancer treatment. Structurally, oxaliplatin features a non-labile chelating R,R-1,2-diaminocyclohexane (DACH) ligand and a labile oxalate group, which dissociates in vivo. Doxorubicin is a chemotherapeutic drug used for treating a broad spectrum of cancers. Structurally, the sugar moiety of doxorubicin (DOX), called daunosamine, provides a versatile platform for platination.

Figure 3:
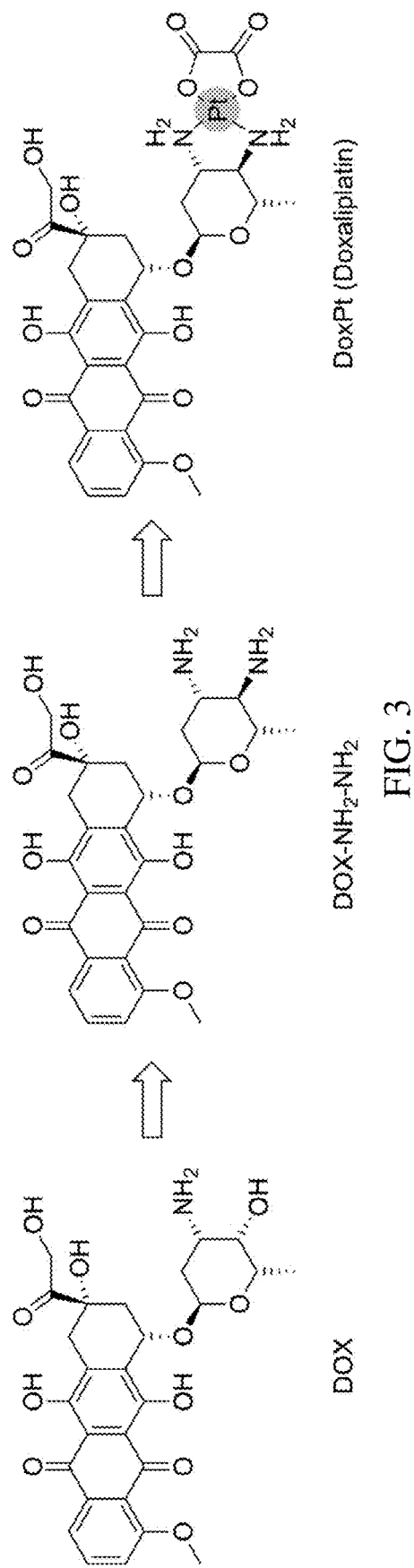
FIG. 3 shows doxorubicin (DOX), DOX-NH$_2$—NH$_2$, and DoxPt (doxaliplatin).

The cis 1,2-amino alcohol unit of the daunosamine was stereoselectively converted to a chelating trans 1,2-diamine motif (FIG. 3, DOX-NH$_2$—NH$_2$), the relative configuration of which matches that of oxaliplatin. Although the absolute configuration of the 1,2-diamino unit is opposite to that of oxaliplatin, it was unexpectedly discovered that the different absolute configuration is not detrimental to the anticancer activity of the designed conjugate (DoxPt, doxaliplatin).

Synthesis

To achieve the desired 4'-dehydroxyamination of DOX, the 3'-amino group and the 9- and 14-hydroxyl groups of DOX were protected. The 3'-amino group was protected with an N-trifluoroacetyl group. A cyclic orthoester was introduced to mask both 9- and 14-hydroxyl groups, essentially a 1,3-diol moiety.

Figure 4:
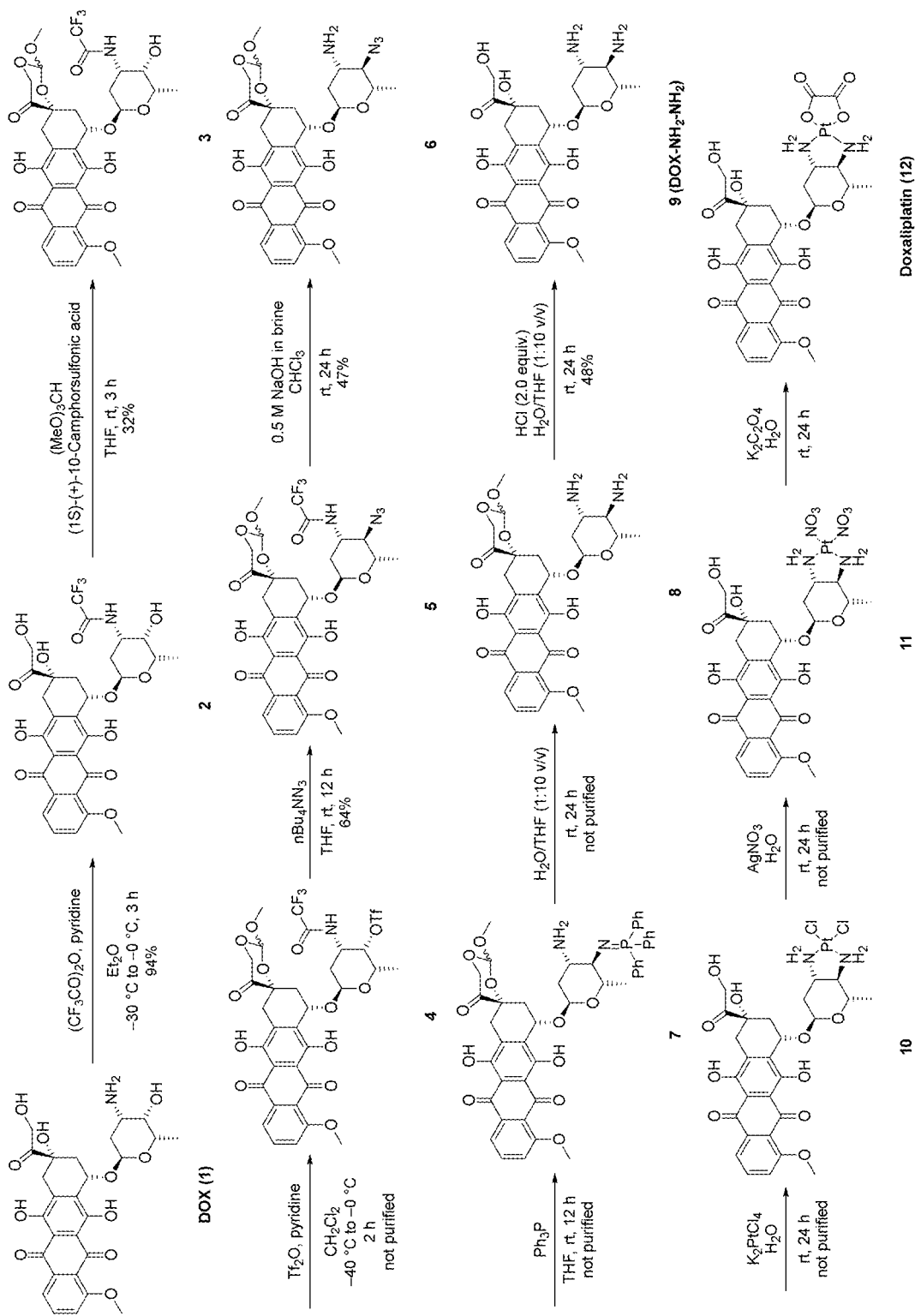
FIG. 4 shows a scheme for the synthesis of doxaliplatin, in accordance with some embodiments.

The synthesis started with the protection of the 3'-amino group by treating DOX hydrochloride with trifluoroacetic anhydride in pyridine (FIG. 4). The N-trifluoroacetylated DOX (2) was subsequently allowed to react with trimethyl orthoformate in the presence of a catalytic amount of (1S)-(+)-10-camphorsulfonic acid to yield compound 3, of which both 9- and 14-hydroxyl groups were protected. As indicated by $^1$H NMR spectroscopy, the obtained orthoester was a mixture of two diastereomers. The lack of stereoselectivity, as described below, did not affect the subsequent synthesis. Compound 3 was then reacted with trifluoromethanesulfonic anhydride and pyridine to give the corresponding 4'-triflate (4). The reaction of 4 with tetra-n-butyl ammonium azide (nBu$_4$NN$_3$) in anhydrous tetrahydrofuran (THF) presumably through an S$_N$2 mechanism afforded 4'-dehydroxyazido compound 5 with the inversion of the stereochemistry at the 4' position. The removal of the N-trifluoroacetyl group of 5 was then performed in a mixture of CHCl$_3$ and 0.5 M NaOH in saturated brine. The resulting product 6 underwent the Staudinger reaction with triphenylphosphine to give the corresponding iminophosphorane (6). The target DOX-NH$_2$—NH$_2$ (9) was obtained through the hydrolysis of the iminophosphorane followed by the HCl-induced deprotection of orthoester. $^1$H NMR spectroscopic studies of 9 confirmed the trans configuration of the 1,2-diamino moiety. The titled platinum complex, doxaliplatin (12), was prepared in a one-pot fashion by sequentially treating compound 9 with K$_2$PtCl$_4$, AgNO$_3$, and K$_2$C$_2$O$_4$.

Cytotoxicity Studies

Figure 5A:
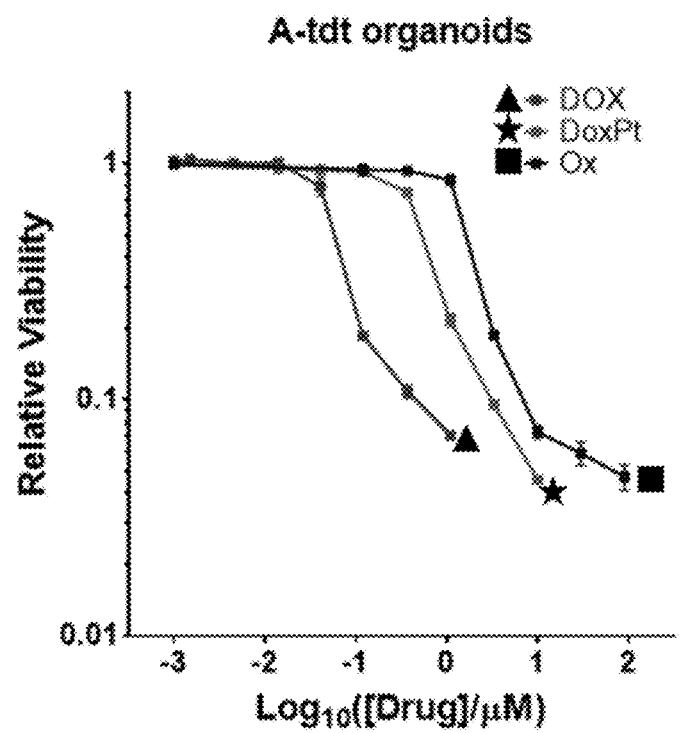
FIGS. 5A-5C show representative dose-response curves showing the effect of oxaliplatin (Ox), doxorubicin (DOX), and doxaliplatin (DoxPt) on the viability of various murine colorectal cancer organoid genotypes after 48 hours of treatment: APC$^{-/-}$; TdTomato$^+$ (A-tdt) organoids (FIG. 5A), APC$^{-/-}$; P53$_{-/-}$; TdTomato$^+$ (AP-tdt) organoids (FIG. 5B), and APC$^{-/-}$; KRAS$^{G12D/WT}$; P53$^{-/-}$; TdTomato$^+$ (AKP-tdt) organoids (FIG. 5C).
Figure 5B:
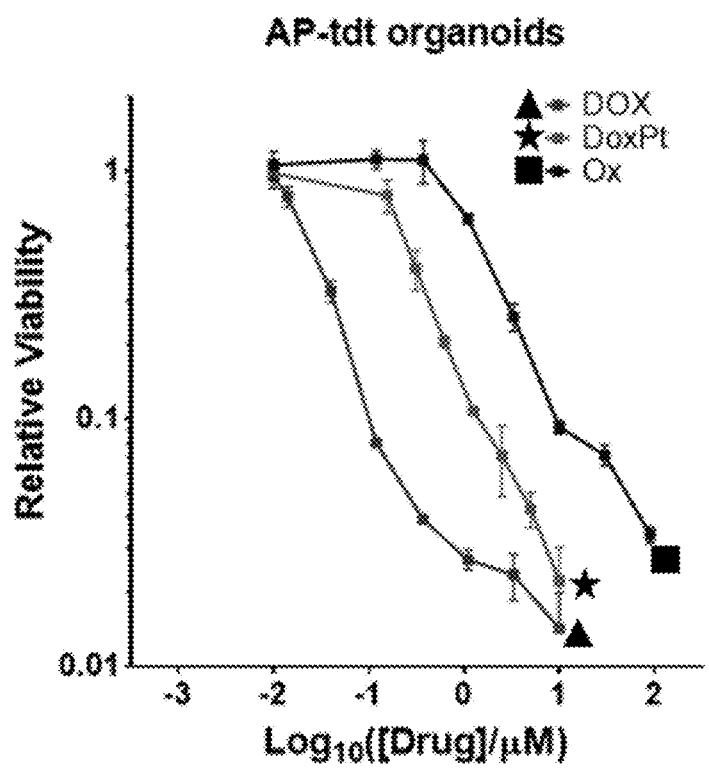
Figure 5C:
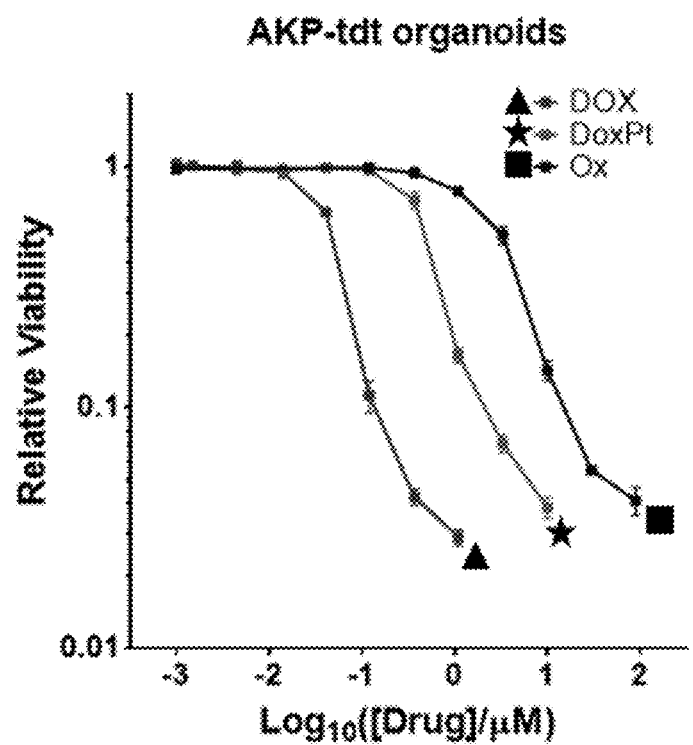

The obtained platinum complex, doxaliplatin, displayed potent anticancer activity across a series of murine colorectal cancer organoids engineered to harbor mutations commonly found in human colon cancer. This organoid series was also engineered to express the fluorescent protein TdTomato, which can facilitate future in vivo studies, and comprises the following genotypes: 1. APC$^{-/-}$; TdTomato$^+$ (A-tdt), 2. APC$^{-/-}$; P53$^{-/-}$; TdTomato$^+$ (AP-tdt), 3. APC$^{-/-}$; KRAS$^{G12D/WT}$; P53$^{-/-}$; TdTomato$^+$ (AKP-tdt), 4. APC$^{-/-}$; KRAS$^{G12D/WT}$; P53$^{-/-}$ (AKP), 5. APC$^{-/-}$; KRAS$^{G12D/WT}$; P53$^{-/-}$; MSH2$^{-/-}$ (AKP-MSH2). Within the series of A-tdt, AP-tdt, and AKP-tdt, doxaliplatin exhibited three to ten-fold higher cellular toxicity than oxaliplatin did against these organoids (FIGS. 5A-5C, Table 1). Importantly, the IC$_{50}$ value of doxaliplatin was largely independent of the genotype of the organoids, suggesting that doxaliplatin may be effective in cancers harboring a variety of different mutations.

TABLE 1

IC$_{50}$ values (μM) and the corresponding 95% confidence intervals (μM, in parentheses) of oxaliplatin (Ox), doxaliplatin (DoxPt), and doxorubicin (DOX) against various murine colorectal cancer organoids after 72-h exposure.

| | A-tdt organoids | AP-tdt organoids | AKP-tdt organoids |
|---|---|---|---|
| Ox | 2.2 (1.9-2.4) | 1.5 (1.2-2.0) | 4.1 (3.4-5.0) |
| DoxPt | 0.46 (0.41-0.51) | 0.41 (0.30-0.58) | 0.43 (0.30-0.65) |
| DOX | 0.058 (0.051-0.065) | 0.045 (0.035-0.059) | 0.075 (0.059-0.097) |

Figure 6:
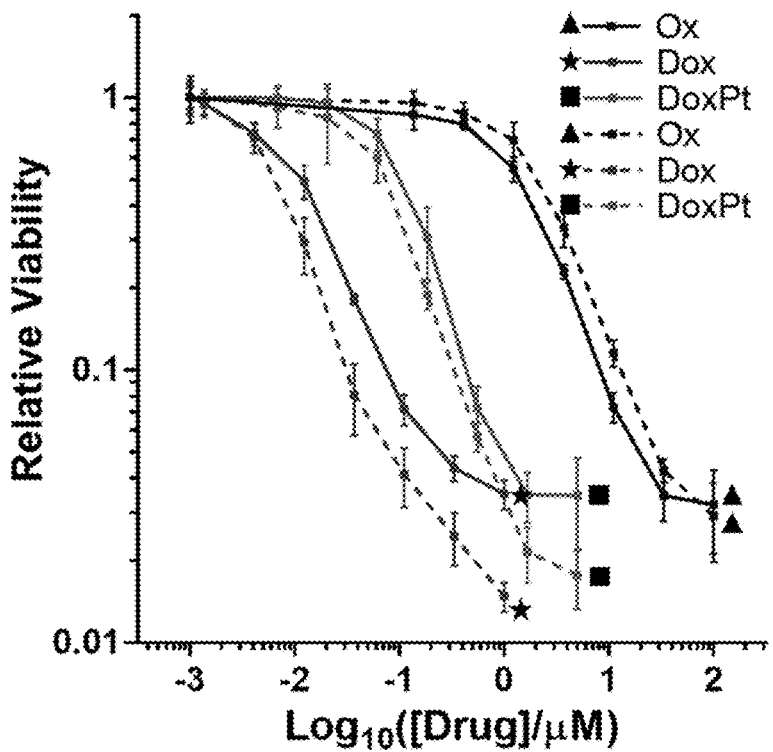
FIG. 6 shows representative dose-response curves showing the effect of oxaliplatin (Ox), doxorubicin (DOX), and doxaliplatin (DoxPt) on the viability of APC$^{-/-}$; KRAS$^{G12D/WT}$; P53$^{-/-}$ (solid lines) and APC$^{-/-}$; KRAS$^{G12D/WT}$; P53$^{-/-}$; MSH2$^{-/-}$ (dashed lines) murine colorectal cancer organoids 72 hours after treatment.
Figure 7A:
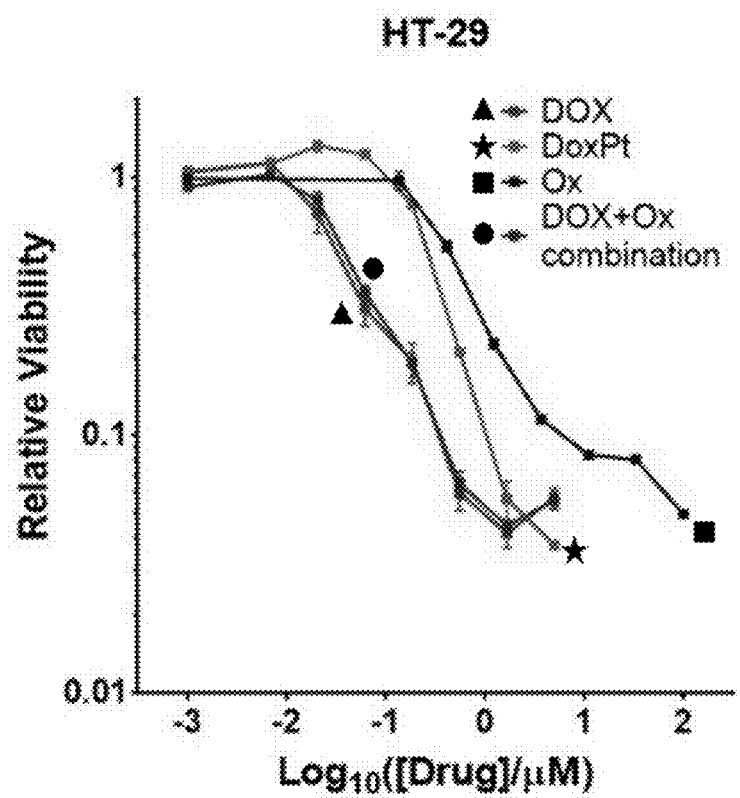
FIGS. 7A-7F show dose-response curves showing the effect of oxaliplatin (Ox), doxorubicin (DOX), doxaliplatin (DoxPt), and a physical mixture of oxaliplatin and doxorubicin (DOX+Ox) on the viability of a series of cancer cell lines 72 hours after treatment: HT-29 human colorectal adenocarcinoma (FIG. 7A), MDA-MB-231 human breast adenocarcinoma (FIG. 7B), PC3 human prostate adenocarcinoma (FIG. 7C), U2OS human osteosarcoma (FIG. 7D), A549 human lung carcinoma (FIG. 7E), and HL60 human leukemia cell line (FIG. 7F).
Figure 7B:
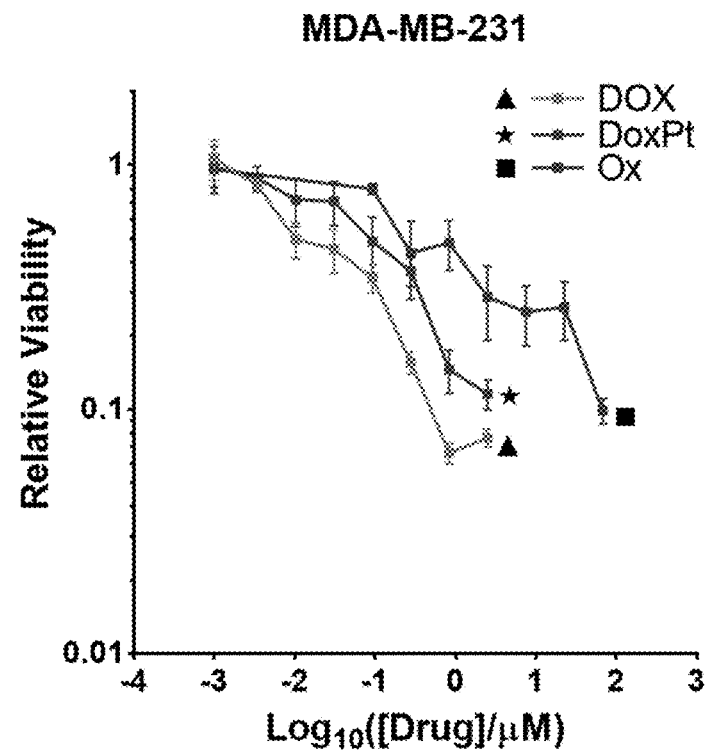
Figure 7C:
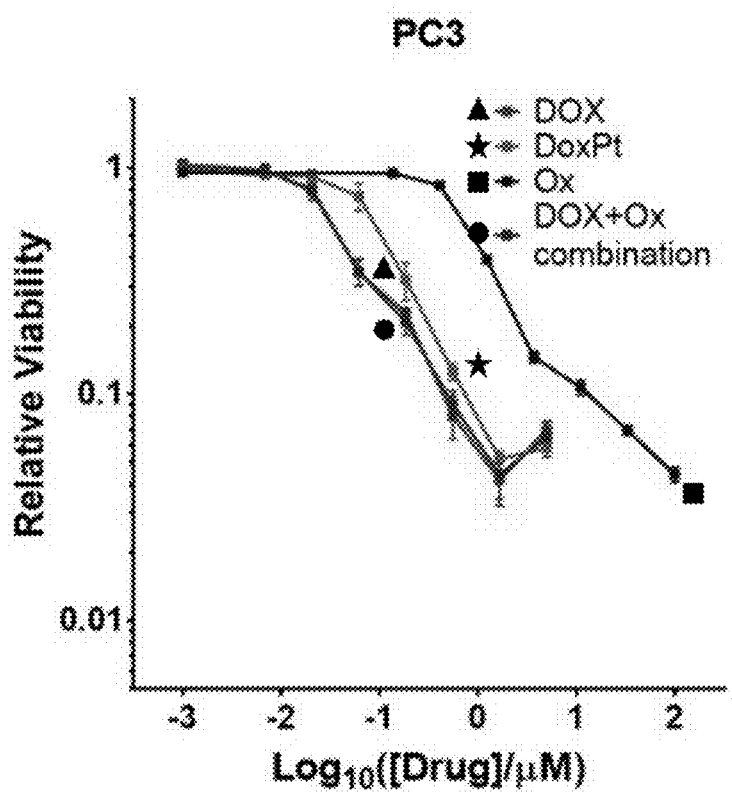
Figure 7D:
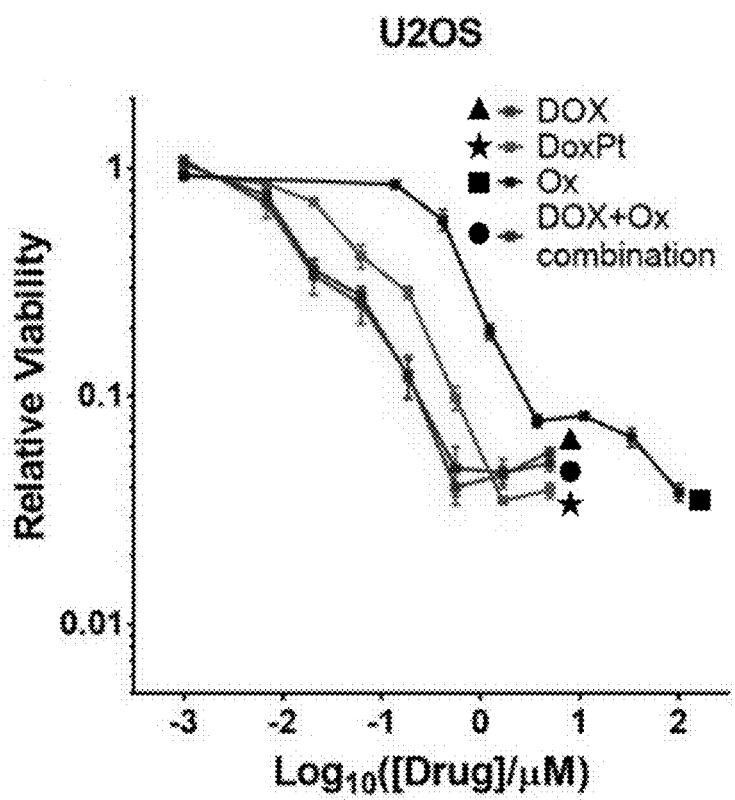
Figure 7E:
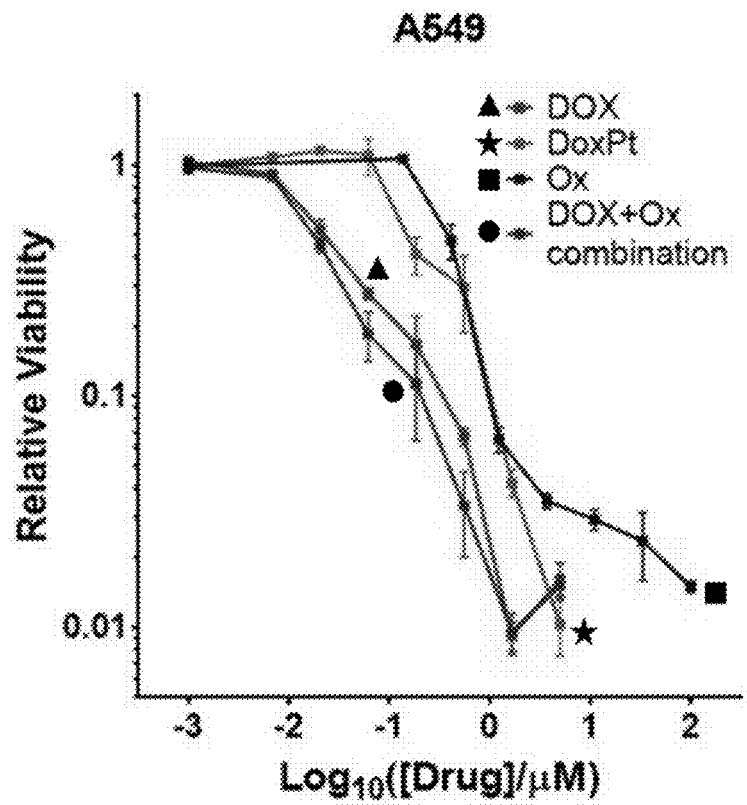
Figure 7F:
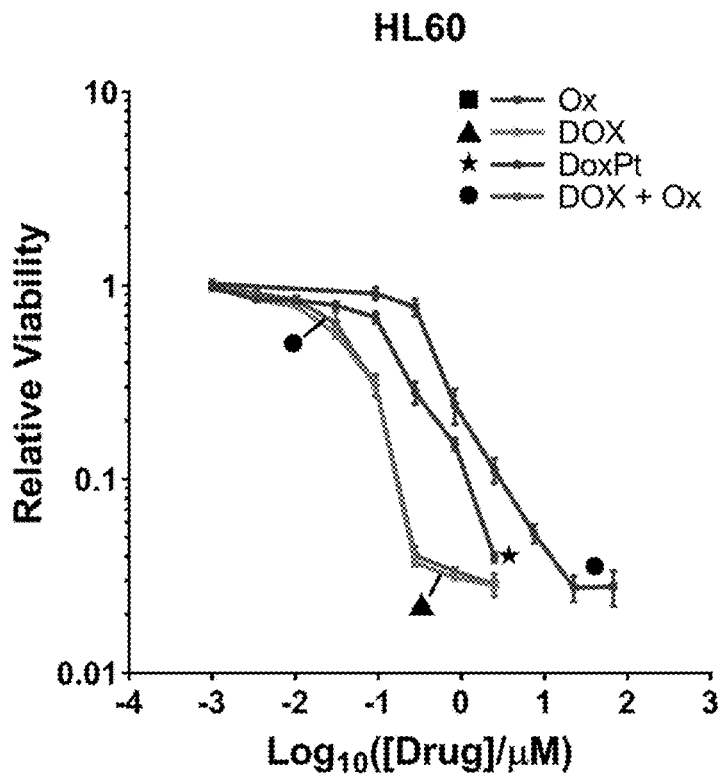
Figure 8A:
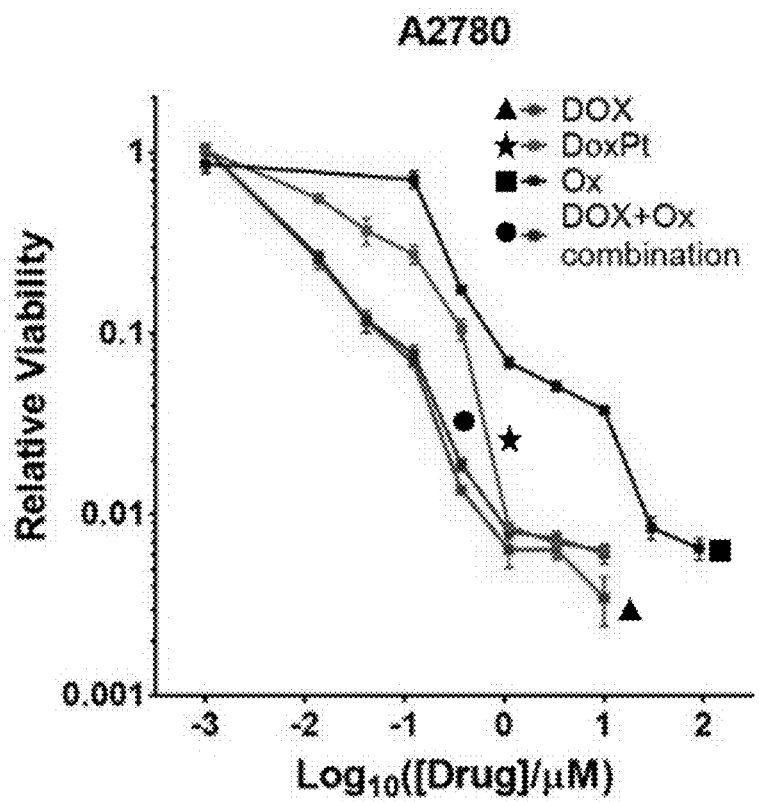
FIGS. 8A-8C show dose-response curves showing the effect of oxaliplatin (Ox), doxorubicin (DOX), doxaliplatin (DoxPt), and a physical mixture of oxaliplatin and doxorubicin (DOX+Ox) on the viability of various cell lines 72 hours after treatment: the A2780 human ovarian cancer cell line (FIG. 8A), the A2780-ADR doxorubicin-resistant human ovarian cancer cell line (FIG. 8B), and the A2780-CIS cisplatin-resistant human ovarian cancer cell line (FIG. 8C).
Figure 8B:
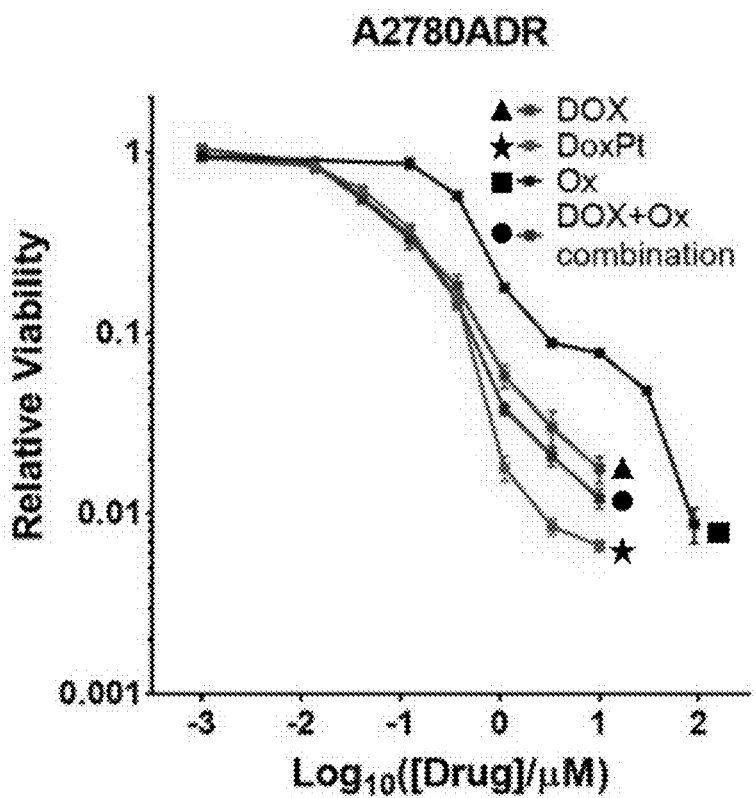
Figure 8C:
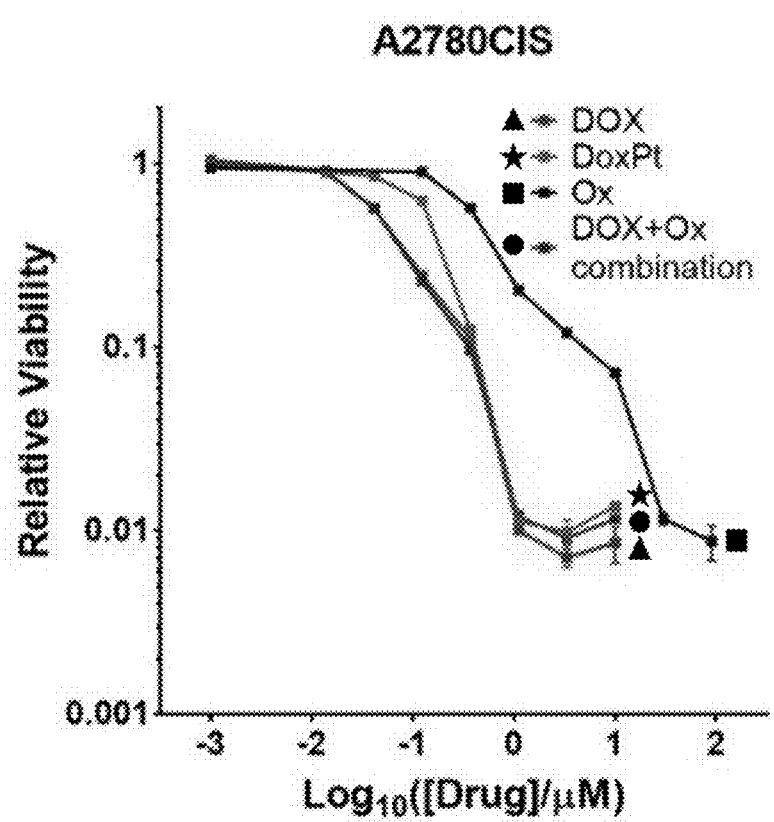

The efficacy of doxaliplatin in the context of microsatellite unstable colon cancer was then investigated, using murine AKP-MSH2 colorectal cancer organoids as a model for microsatellite unstable colon cancers. Compared to AKP control organoids, AKP-MSH2 organoids were modestly resistant to oxaliplatin, but displayed increased sensitivity to doxaliplatin and doxorubicin (FIG. 6). As measured by IC$_{50}$ values, doxaliplatin was 13-fold and 28-fold more potent than oxaliplatin in killing AKP and AKP-MSH2 organoids, respectively (Table 2). The above observations support the potential of using doxaliplatin as a drug candidate for advanced cancers harboring multiple oncogenic mutations, including micsrosatellite unstable colorectal cancers, and especially those cancers harboring mutations causing resistance to conventional platinum drugs.

TABLE 2

IC$_{50}$ values (μM) and the corresponding 95% confidence
intervals (μM, in parentheses) of oxaliplatin (Ox),
doxaliplatin (DoxPt), and doxorubicin (DOX) against AKP
and AKP-MSH2 colorectal cancer organoids after 72-h exposure.

|       | AKP organoids       | AKP-MSH2 organoids    |
|-------|---------------------|------------------------|
| Ox    | 1.4 (1.1-1.8)       | 2.2 (1.8-2.6)          |
| DoxPt | 0.11 (0.091-0.13)   | 0.078 (0.058-0.10)     |
| DOX   | 0.0091 (0.0066-0.011)| 0.0065 (0.0051-0.0078)|

The activity of doxaliplatin was studied against a panel of cell lines (FIGS. 7A-7F). According to IC$_{50}$ values, doxaliplatin generally exhibited 1.4 to 11-fold higher potency than oxaliplatin across six cell lines tested (Table 3). The activity of doxaliplatin was investigated in the A2780 human ovarian cancer cell line, the doxorubicin-resistant variant A2780ADR cell line, and the cisplatin-resistant variant A2780CIS cell line. As observed in the colorectal cancer organoids, doxaliplatin was also significantly more potent than oxaliplatin (FIG. 6, Table 4). Importantly, as indicated by IC$_{90}$ and IC$_{95}$ values, although A2780ADR conferred significant resistance to oxaliplatin and doxorubicin, singly or in combination, this cell line responded fully to doxaliplatin treatment (FIG. 6 and Table 5). Moreover, A2780ADR was cross-resistant to oxaliplatin (Tables 4 and 5), indicating that resistance to oxaliplatin did not confer resistance to doxaliplatin. Thus, doxaliplatin may also be effective in treating oxaliplatin-resistant cancers. The remarkable ability of doxaliplatin to overcome drug resistance was also evidenced by its ability to inhibit growth A2780CIS cells effectively.

Figure 9A:
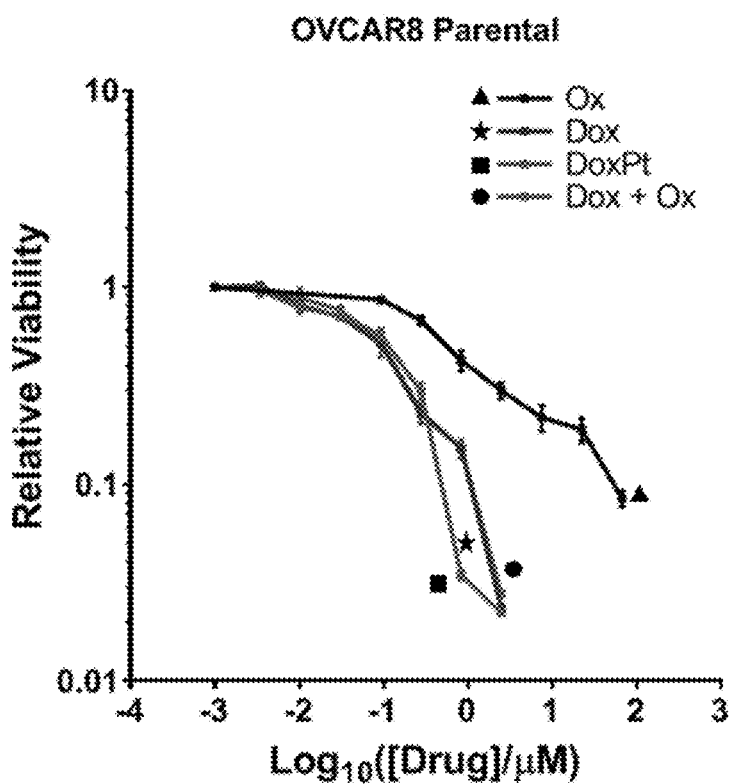
FIGS. 9A-9B show dose-response curves showing the effect of oxaliplatin (Ox), doxorubicin (DOX), doxaliplatin (DoxPt), and a physical mixture of oxaliplatin and doxorubicin (DOX+Ox) on the viability of the OVCAR8 human ovarian cancer cell line (FIG. 9A) and the OVCAR8-OXR oxaliplatin-resistant human ovarian cancer cell line (FIG. 9B).
Figure 9B:
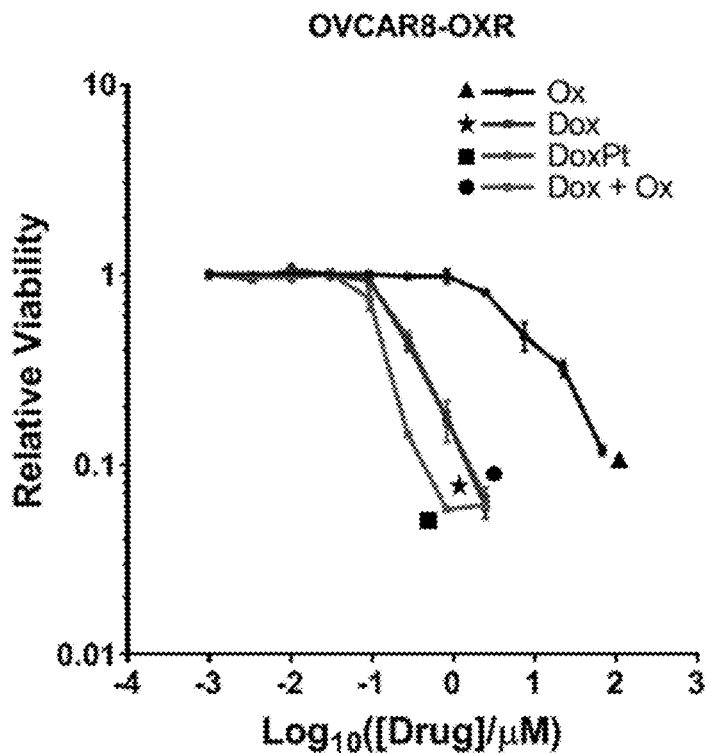

In addition, an oxaliplatin-resistant ovarian cancer line, OVCAR8-OXR, was generated by exposing the parental OVCAR8 cells repeatedly with oxaliplatin. As shown in FIGS. 9A-9B and Table 7, based on the IC$_{50}$ values, the OVCAR8-OXR cells conferred a 14-fold resistance to oxaliplatin and a modest cross-resistance to doxorubicin or a physical combination of doxorubicin and oxaliplatin. In contrast, the OVCAR8-OXR cells remained sensitive toward the covalent drug conjugate, doxaliplatin, which showed no change in the IC$_{50}$ value. A similar conclusion was also drawn by comparing the IC$_{80}$ values of the drugs against OVCAR8 and OVCAR8-OXR cells (Table 8). Taken together, these observations suggested that doxaliplatin can treat doxorubicin-resistant or conventional platinum agent-resistant ovarian cancers and possibly other doxorubicin or platinum-resistant cancers.

TABLE 3

IC$_{50}$ values (μM) of oxaliplatin (Ox), doxaliplatin (DoxPt), doxorubicin
(DOX), and a physical mixture of oxaliplatin and doxorubicin
(DOX + Ox) against various cancer cell lines after 96-h exposure.

|          | HT-29 (colon) | MDA-MB-231 (breast) | PC3 (prostate) | U2OS (bone) | A549 (lung) | HL60 (leukemia) |
|----------|---------------|---------------------|----------------|-------------|-------------|------------------|
| Ox       | 0.47          | 0.92                | 1.0            | 0.58        | 0.40        | 0.56             |
| DoxPt    | 0.33          | 0.11                | 0.092          | 0.052       | 0.10        | 0.16             |
| DOX      | 0.038         | 0.075               | 0.041          | 0.013       | 0.023       | 0.043            |
| DOX + Ox | 0.046         | —                   | 0.048          | 0.012       | 0.020       | 0.055            |

TABLE 4

IC$_{50}$, IC$_{90}$, and IC$_{95}$ values (μM) of oxaliplatin (Ox),
doxaliplatin (DoxPt), doxorubicin (DOX), and a physical
mixture of oxaliplatin and doxorubicin (DOX + Ox) against
the A2780 human ovarian cancer cell line after 72-h exposure.

|          | IC$_{50}$ | IC$_{90}$ | IC$_{95}$ |
|----------|-----------|-----------|-----------|
| Ox       | 0.17      | 0.59      | 5.6       |
| DoxPt    | 0.016     | 0.38      | 0.68      |
| DOX      | 0.011     | 0.075     | 0.16      |
| DOX + Ox | 0.011     | 0.083     | 0.18      |

TABLE 5

IC$_{50}$, IC$_{90}$, and IC$_{95}$ values (μM) of oxaliplatin (Ox), doxaliplatin
(DoxPt), doxorubicin (DOX), and a physical mixture of oxaliplatin
and doxorubicin (DOX + Ox) against the doxorubicin-resistant
A2780ADR human ovarian cancer cell line after 72-h exposure.

|          | IC$_{50}$ | IC$_{90}$ | IC$_{95}$ |
|----------|-----------|-----------|-----------|
| Ox       | 0.43      | 2.4       | 29        |
| DoxPt    | 0.072     | 0.49      | 0.67      |
| DOX      | 0.054     | 0.62      | 1.6       |
| DOX + Ox | 0.053     | 0.51      | 2.4       |

TABLE 6

IC$_{50}$, IC$_{90}$, and IC$_{95}$ values (μM) of oxaliplatin (Ox), doxaliplatin
(DoxPt), doxorubicin (DOX), and a physical mixture of oxaliplatin
and doxorubicin (DOX + Ox) against the cisplatin-resistant
A2780CIS human ovarian cancer cell line after 72-h exposure.

|          | IC$_{50}$ | IC$_{90}$ | IC$_{95}$ |
|----------|-----------|-----------|-----------|
| Ox       | 0.43      | 6.6       | 13        |
| DoxPt    | 0.28      | 0.38      | 0.41      |
| DOX      | 0.050     | 0.39      | 0.54      |
| DOX + Ox | 0.049     | 0.36      | 0.49      |

TABLE 7

IC$_{50}$ values (μM) of oxaliplatin (Ox), doxaliplatin (DoxPt),
doxorubicin (DOX), and a physical mixture of oxaliplatin
and doxorubicin (DOX + Ox) against the OVCAR8 and OVCAR8-OXR
human ovarian cancer cell line after 72-h exposure.

| IC$_{50}$ (μM) | OVCAR8        | OVCAR8OXR     | Fold Resistance |
|----------------|---------------|---------------|-----------------|
| DOX            | 0.086 ± 0.003 | 0.25 ± 0.01   | 2.9             |
| Ox             | 0.58 ± 0.06   | 8.2 ± 1.3     | 14              |
| DOX + Ox       | 0.10 ± 0.01   | 0.27 ± 0.01   | 2.7             |
| DoxPt          | 0.14 ± 0.01   | 0.14 ± 0.01   | 1.0             |

TABLE 8

IC$_{80}$ values (μM) of oxaliplatin (Ox), doxaliplatin (DoxPt),
doxorubicin (DOX), and a physical mixture of oxaliplatin
and doxorubicin (DOX + Ox) against the OVCAR8 and OVCAR8-OXR
human ovarian cancer cell line after 72-h exposure.

| IC$_{80}$ (μM) | OVCAR8       | OVCAR8OXR    | Fold Resistance |
|----------------|--------------|--------------|-----------------|
| DOX            | 0.41 ± 0.02  | 0.74 ± 0.05  | 1.8             |
| Ox             | 12 ± 3       | 40 ± 2       | 3.3             |
| DOX + Ox       | 0.41 ± 0.02  | 0.78 ± 0.08  | 1.9             |
| DoxPt          | 0.37 ± 0.02  | 0.23 ± 0.01  | 0.6             |

Platinum Uptake

Figure 10:
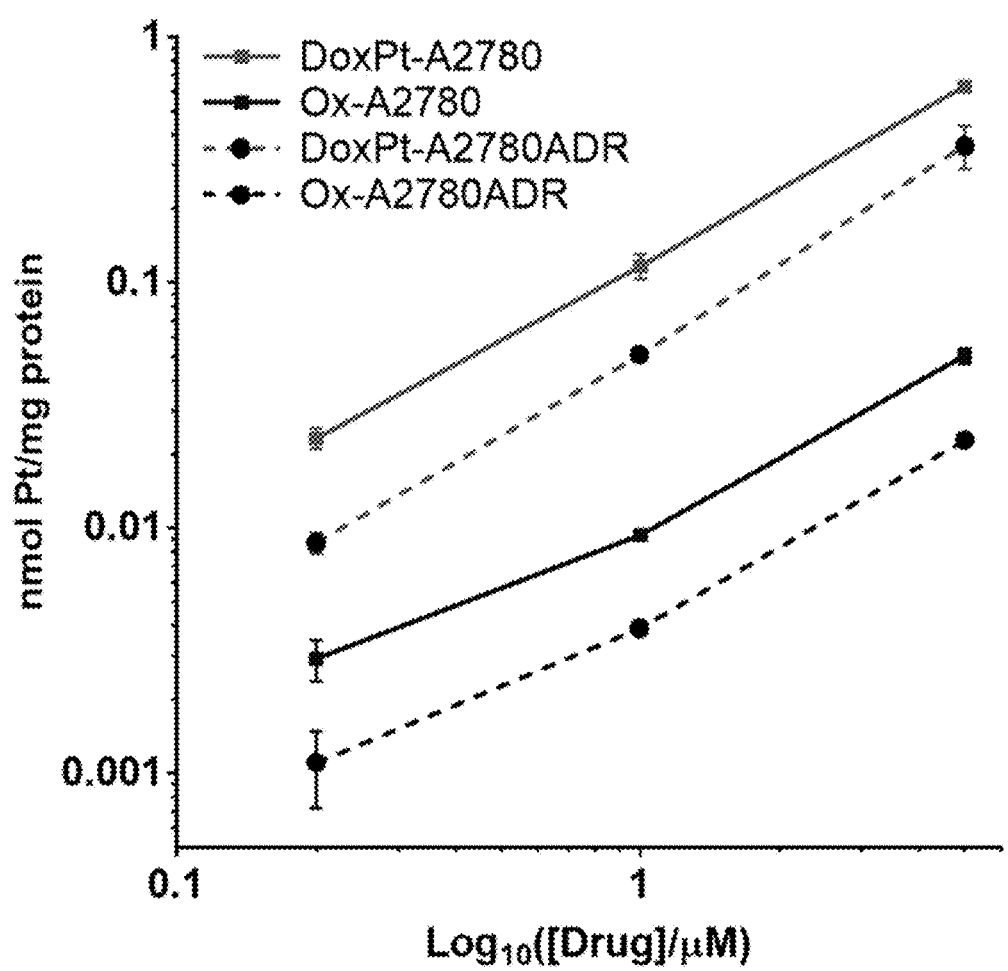
FIG. 10 shows the inductively coupled plasma mass spectrometry (ICP-MS) determined platinum uptake by the A2780 ovarian cancer cell line and the doxorubicin-resistant A2780ADR ovarian cancer cell line. The cells were treated with the corresponding platinum agent at the indicated concentration for three hours. Solid lines show the uptake of oxaliplatin (Ox) and doxaliplatin (DoxPt) in A2780 cells. Dashed lines show the uptake of oxaliplatin (Ox) and doxaliplatin (DoxPt) in A2780ADR cells.

The whole-cell platinum uptake of oxaliplatin and doxaliplatin was investigated under different conditions using inductively coupled plasma mass spectrometry (ICP-MS). As shown in FIG. 10, the platinum uptake was linearly dependent on the concentration of the drug during the treatment. Platinum content was attenuated by about 50% in doxorubicin-resistant A2780ADR cells, as compared to that in the non-resistant A2780 cells (Table 9). The decreased platinum accumulation may in part explain the relatively lower susceptibility of A2780ADR cells to platinum treatment than that of A2780 cells. More importantly, regardless of cell types, the platinum concentration in doxaliplatin-treated cells was approximately ten times higher than in oxaliplatin-treated cells (Table 9), which may contribute to the high anticancer activity of doxaliplatin.

TABLE 9

Platinum drug uptake (nmol/mg protein) by A2780 human ovarian cancer cell line and its doxorubicin-resistant variant A2780ADR at drug concentrations during the treatment.

| [Drug] (μM) | A2780 treated with Ox | A2780 treated with DOX | A2780ADR treated with Ox | A2780ADR treated with DOX |
|---|---|---|---|---|
| 0.00 | 0.0020 ± 0.0002 | | 0.00038 ± 0.00045 | |
| 0.20 | 0.0029 ± 0.0006 | 0.023 ± 0.002 | 0.0011 ± 0.0004 | 0.0087 ± 0.0008 |
| 1.0 | 0.0093 ± 0.0004 | 0.12 ± 0.01 | 0.0039 ± 0.0001 | 0.051 ± 0.001 |
| 5.0 | 0.050 ± 0.004 | 0.63 ± 0.03 | 0.023 ± 0.001 | 0.36 ± 0.07 |

Figure 11:
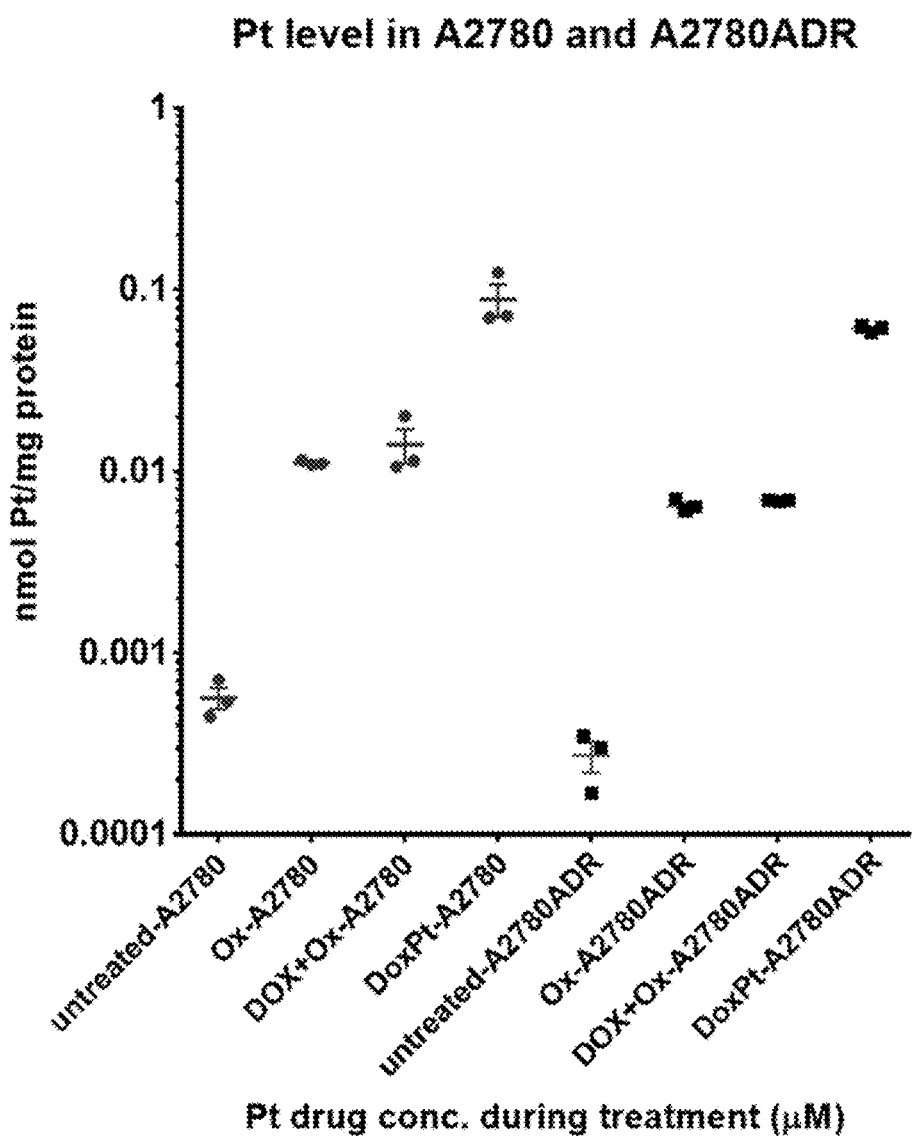
FIG. 11 shows a comparison of the accumulation of doxaliplatin alone, oxaliplatin alone, and a mixture of oxaliplatin and doxorubicin. The platinum uptake by A2780 ovarian cancer cell line and doxorubicin-resistant A2780ADR ovarian cancer cell line was determined by ICP-MS. The cells were treated with the indicated single drug at 1.0 µM or a mixture of oxaliplatin (1.0 µM) and doxorubicin (1.0 µM) for three hours. Uptake in A2780 and A2780ADR cells is indicated by circle and square data points, respectively.

It was further explored whether high drug accumulation of the covalent conjugate, doxaliplatin, could be attained by using a physical mixture of doxorubicin and oxaliplatin. In this separate experiment, the platinum content in A2780 cells and A2780ADR cells treated with oxaliplatin alone or a 1:1 combination of oxaliplatin and doxorubicin were compared (Table 10). As shown in FIG. 11, physically mixing oxaliplatin with doxorubicin exerted minimal effects in platinum uptake. This observation manifested the advantage of covalent drug conjugation over physical drug mixing and indicated that the unique pharmaceutical profile of doxaliplatin is unlikely to be achieved using a combination of oxaliplatin and doxorubicin.

TABLE 10

Comparison of platinum drug uptake (nmol/mg protein) of doxaliplatin, oxaliplatin alone, and a physical mixture of oxaliplatin with doxorubicin.

| Drug | A2780 | A2780ADR |
|---|---|---|
| untreated | 0.00057 ± 0.00013 | 0.00027 ± 0.00009 |
| Ox | 0.011 ± 0.000 | 0.0065 ± 0.0004 |
| Ox + DOX | 0.014 ± 0.005 | 0.0070 ± 0.0000 |
| DoxPt | 0.089 ± 0.031 | 0.061 ± 0.003 |

CONCLUSION

In summary, a synthetic route that facilitated the platination of a doxorubicin derivative through a non-cleavable bidentate binding mode was demonstrated. Exploiting this synthetic protocol, a novel platinum agent, doxaliplatin, which displayed a significantly enhanced anticancer profile compared to oxaliplatin and doxorubicin, singly or in combination, was obtained. The improvement was particularly substantial when treating doxorubicin- or oxaliplatin-resistant cell lines. It is unequivocal that the synthetic schemes devised en route to doxaliplatin may facilitate conjugation of other anthracyclines to platinum agents used in the clinic.

Experimental Section
Materials and Methods.

Reagents were purchased from commercial sources and used as received. Doxorubicin hydrochloride was purchased from A Chemtek Inc. and its purity was examined by $^1$H NMR spectroscopy and analytical HPLC. Anhydrous solvents were saturated with argon and purified by passage through two columns of activated alumina. Air-sensitive reactions and compounds were handled with standard Schlenk techniques or in an MBraun dry box. Column chromatography was performed on silica gel (230-400 mesh, 60 Å).

The title platinum-containing compound was purified by a reverse phase Biotage® SNAP Ultra C18 column (12 g) using $H_2O$/MeOH as the mobile phase prior to HPLC purification. Compound 9 (DOX-$NH_2$—$NH_2$) and doxaliplatin were purified using Agilent 1260 Series HPLC systems fitted with multi-wavelength detectors using a C18 reverse stationary phase (Zorbax-SB C18 column: 7 μm, 21.2×250 mm). The purity of compound 9 and doxaliplatin was examined using an Agilent 1200 Series HPLC system fitted with multi-wavelength detectors using a C18 reverse stationary phase (Zorbax-SB C18 column: 5 μm, 4.6×250 mm). The mobile phase was composed of two solvents. For 9, the mobile phase was composed of A: $H_2O$+0.1% (v/v) $CF_3CO_2H$; B: $CH_3CN$+0.1% (v/v) $CF_3CO_2H$. For doxaliplatin, the mobile phase was composed of A: $H_2O$; B: $CH_3OH$.

NMR spectra were acquired on a 400 MHz Bruker AVANCE-400 spectrometer or a Varian Inova-500 NMR spectrometer. $^1$H NMR and $^{13}$C NMR chemical shifts are reported in ppm relative to that of $SiMe_4$ (δ=0.00) and were referenced internally to residual solvent peaks.[31] $^{195}$Pt NMR chemical shifts were reported in ppm relative to that of $K_2PtCl_6$ (δ=0.00). Low-resolution electrospray mass spectra were acquired on an Agilent 1100 Series LC/MSD Trap spectrometer. High-resolution mass spectra were acquired on an Agilent 6510 Series Quadrupole Time-Of-Flights spectrometer at the MIT Center for Environmental Health Sciences. MS/MS mass spectra were acquired on an Agilent 6410 Triple Quadrupole LC/MS at a fragmentor voltage of 202.0V and a collisionally induced dissociation of 40.0 eV at the MIT Center for Environmental Health Sciences.

ICP-MS was performed on an Agilent 7900 ICP-MS in helium mode. The ICP-MS was equipped with an integrated auto-sampler at the MIT CEHS core facility.

Colorectal Cancer Organoid Generation, and Testing of Oxaliplatin, Doxorubicin, and Doxaliplatin Colonic crypts were isolated and colon organoids were generated from the following mouse genotypes on a C57Bl/6 background: 1. Rosa-LSL-TdTomato (hereafter LSL-tdt), 2. P53$^{fl/fl}$; LSL-tdt, and 3. LSL-KRAS$^{G12D/WT}$; P53$^{fl/fl}$; LSL-tdt mice. Subsequently, the pSECC-APC plasmid (carrying Cre, Cas9, and sgAPC) was transfected into each of the above three genotypes of colon organoids. This transfection strategy generated, in a single step, the following colorectal cancer organoids, including 1. APC$^{-/-}$; TdTomato$^+$ (A-tdt), 2. APC$^{-/-}$; P53$^{-/-}$; TdTomato$^+$ (AP-tdt), and 3. APC$^{-/-}$; KRAS$^{G12D/WT}$; P53$^{-/-}$; TdTomato$^+$ (AKP-tdt). Organoids of the desired genotype were selected for by Wnt/Rspo withdrawal for APC$^{-/-}$, Nutlin-3 addition for P53$^{-/-}$, and EGF withdrawal for KRAS$^{G12D}$.

To generate 4. APC$^{-/-}$; KRAS$^{G12D/WT}$; P53$^{-/-}$; (AKP) and 5. APC$^{-/-}$; KRAS$^{G12D/WT}$; P53$^{-/-}$; MSH2$^{-/-}$ (AKP-MSH2) colon cancer organoids, colonic crypts were isolated and colon organoids were generated from the following mouse genotypes on a C57Bl/6 background: 4. LSL-KRAS$^{G12D/WT}$; P53$^{fl/fl}$ mice and 5. LSL-KRAS$^{G12D}$; P53$^{fl/fl}$; MSH2$^{fl/fl}$ mice. Subsequently, the pSECC-APC plasmid (carrying Cre, Cas9, and sgAPC) was transfected into each of the above two genotypes of colon organoids. Following pSECC-APC transfection, Wnt/Rspo withdrawal was performed and surviving (APC$^{-/-}$) single organoids were cloned and PCR genotyped for Cre mediated deletion of p53 and/or MSH2, and for Cre mediated activation of oncogenic KRAS$^{G12D}$.

To determine IC$_{50}$ values for oxaliplatin, doxorubicin, and doxaliplatin in A-tdt, AP-tdt, and AKP-tdt organoids, organoids were trypsinized and seeded in 10 µL drops of 67% Corning Matrigel (growth factor reduced) with 33% culture media described below. Twenty four hours after seeding the organoids, a media change was performed and dose responses of oxaliplatin, doxorubicin and doxaliplatin were added. Forty eight hours after treatment, cell growth was evaluated by resazurin assay. Organoids were cultured in Advanced DMEM/F12 supplemented with 2 mM GlutaMAX, 1% Penicillin-Streptomycin, 2% B27, and Y-27632 (10 µM).

Testing Oxaliplatin, Doxorubicin, and Doxaliplatin in Cell Lines

Cells were cultured in 10 mL of Advanced DMEM/F12 (ADMEM/F12), supplemented with 5% FBS, 2 mM GlutaMAX, and 1% Penicillin-Streptomycin in 10 cm tissue culture plates. Cells were then plated into 96-well plates with about 2.5×10$^3$ cells per well. Cells were plated with 200 µL per well of ADMEM/F12 supplemented with 5% FBS, 2 mM GlutaMAX, and 1% Penicillin-Streptomycin. Cells were treated with dose responses of doxorubicin, oxaliplatin, or doxaliplatin upon plating. The cells were then cultured for 72 hours following drug treatment, and cell growth was measured by resazurin assay.

Determining Platinum Uptake Using ICP-MS

The cells in a six-well plate were treated with oxaliplatin, doxaliplatin, or a mixture of doxorubicin and oxaliplatin at indicated concentration in 2 mL of Advanced DMEM/F12 (ADMEM/F12), supplemented with 5% FBS, 2 mM GlutaMAX, and 1% Penicillin-Streptomycin. After three hours, the media were removed. The cells were washed with xl PBS buffer containing EDTA (100 µM, 4 mL×2). To each well, MilliQ water (1.0 mL) was added. After 15 min, the cells were suspended. A portion of the resulting cell lysate (900 µL) was transferred to an Eppendorf tube. The samples were frozen in liquid nitrogen and thawed at room temperature. This procedure was repeated for three times. The insoluble lysate was pelleted (10000 rpm for 10 min). The soluble protein concentration was determined using Pierce® 660 nm Protein assay in a 96-well plate as described below. Pierce 660 nm Protein solution (200 µL) was added to each well. An aliquot of the lysate (14.2 µL) was added to each well. The plate was shaken and read on a plate reader. The remaining samples were frozen at liquid nitrogen temperature and lyophilized. The dried material was digested with Aristar® ultrapure concentrated nitric acid (70%) at 70° C. for one hour. An aliquot of this solution (142 µL) was mixed with molecular biology grade water (2000 µL) and a terbium internal standard (40 µL, 100 ppb). The platinum content was then determined using an Agilent 7900 ICP-MS in helium mode. The concentration of platinum in the cells was normalized to measured protein concentration described above.

Synthetic Procedures

A-Trifluoroacetyl Doxorubicin (2)

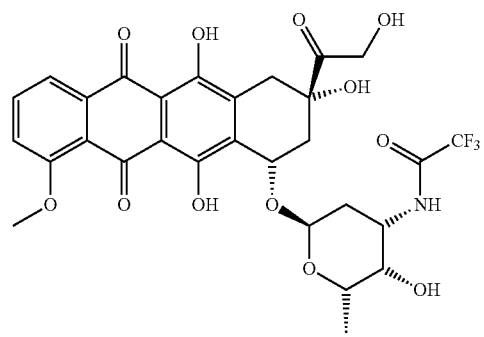

In a Schlenk flask containing doxorubicin hydrochloride salt (1.16 g, 2.0 mmol), anhydrous pyridine (60 mL) was added at −30° C. The reaction was stirred at this temperature for 15 min. A mixture of trifluoroacetic anhydride (3.78 g, 2.54 mL, 18.0 mmol) in Et$_2$O (12 mL) was added to the flask dropwise at the same temperature. The reaction was gradually warmed to 0° C. over a period of 3 h, during which doxorubicin dissolved to give a slightly brown solution. The reaction was diluted with water (100 mL) and stirred for 20 min to hydrolyze excess trifluoroacetic anhydride. The reaction mixture was extracted with ethyl acetate (100 mL×3). The combined organic phase was washed with water (100 mL×3) and dried over MgSO$_4$. The solvent was removed under vacuum. The crude product was suspended in a mixture of butanone and hexanes (80 mL+320 mL, respectively) and stored at −40° C. for 3 h. The dark red solid was collected by suction filtration, washed with hexanes, and dried under vacuum (1.20 g, 94% yield). $^1$H and $^{19}$F NMR spectra indicated that, presumably due to the slow amide bond rotation, two conformers were present in DMSO-d$_6$ with a ratio of 4:1. $^1$H NMR (400 MHz, DMSO-d$_6$) δ 13.98 (s, 1.0H), 13.20 (s, 1.2H), 9.06-9.08 (m, 1.4H), 8.62-8.50 (m, 0.3H), 7.93-7.75 (m, 3.0H), 7.67-7.55 (m, 1.3H), 7.41-7.38 (m, 0.3H), 5.43 (s, 1.0H), 5.24-5.20 (s, 1.5H), 4.99 (d, J=5.9 Hz, 1.2H), 4.91 (dd, J=5.3, 2.8 Hz, 0.9H), 4.85 (t, J=5.9 Hz, 0.9H), 4.58 (d, J=5.9 Hz, 2.0H), 4.22 (q, J=6.3 Hz, 1.0H), 4.09-3.77 (m, 5.0H), 3.52 (d, J=3.9 Hz, 0.8H), 2.91 (dd, J=45.7, 18.2 Hz, 2.0H), 2.26-1.95 (m, 3.5H), 1.47 (dd, J=12.2, 4.1 Hz, 1.0H), 1.18-1.07 (m, 4.0H). $^{19}$F NMR (396 MHz, DMSO-d$_6$) −73.94 (s, 3F), −73.99 (s, 0.84F). ESI-MS(−) m/z calcd for [M−H]$^-$ 638.1, found 638.0.

N-Trifluoroacetyl doxorubicin 9,14-cyclic methyl orthoester (3)

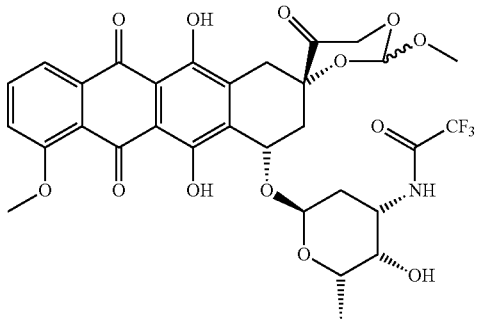

To a solution of 2 (1.06 g, 1.66 mmol) and methyl orthoformate (80 mL) in THF (280 mL) was added (1S)-(+)-10-camphorsulfonic acid (102 mg, 0.44 mmol) in one portion. The reaction was stirred at room temperature for 3 h. The reaction was then quenched with 5 wt % NaHCO$_3$ aq. solution (400 mL). The mixture was extracted with ethyl acetate (100 mL×3). The combined organic phase was washed with 5 wt % NaHCO$_3$ aq. solution (200 mL) and water (200 mL). The organic phase was dried over MgSO$_4$. The solvent was removed under vacuum. The crude product was purified by column chromatography (silica gel, ethyl acetate:hexanes=3:1 to 6:1) to afford a dark orange solid (362 mg, 32% yield). ESI-MS(−) m/z calcd for [M−H]$^−$ 680.2, found 680.1. $^{19}$F NMR spectrum of 3 in acetone-d$_6$ displayed four major signals with a ratio of 70:18:7:5. These signals appeared to correspond to two diastereomers of the cyclic methyl orthoester, each of which has two conformers due to the slow amide bond rotation.

N-Trifluoroacetyl (4'S)-triflate doxorubicin 9,14-cyclic methyl orthoester (4)

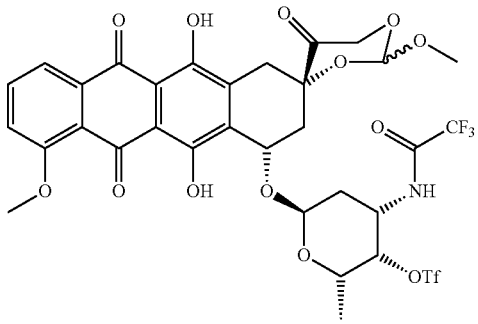

To a Schlenk flask containing 3 (301 mg, 0.44 mmol) in CH$_2$Cl$_2$ (10 mL), pyridine (280 mg, 285 μL, 3.54 mmol) was added dropwise at −40° C. Triflic anhydride (499 mg, 297 μL, 1.77 mmol) in CH$_2$Cl$_2$ (5 mL) was then added dropwise to the flask at the same temperature. The reaction was stirred for 2 h, during which the reaction was gradually warmed to 0° C. The completion of the reaction was confirmed by thin layer chromatography (ethyl acetate:hexanes=3:1). The reaction was diluted with ice water (40 mL). The mixture was extracted with cold Et$_2$O (40 mL×3). The combined organic phase was washed with cold NaOAc aq. solution (10 wt %, 80 mL) and then cold water (80 mL). The organic phase was dried over MgSO$_4$. The solvent was removed under vacuum. The crude product (346 mg) was used in the next step without further purification.

N-Trifluoroacetyl (4'R)-azido doxorubicin 9,14-cyclic methyl orthoester (5)

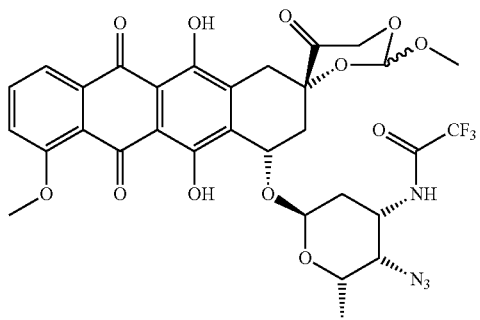

In the glovebox, 4 (crude, 346 mg, approximately 0.43 mmol) was dissolved in anhydrous THF (15) mL). To this solution, nBu$_4$NN$_3$ (121 mg, 0.43 mmol) was added. A dark red solution formed immediately. The reaction was stirred at room temperature for 12 h. The solvent was removed under vacuum. The crude product was purified by column chromatography (ethyl acetate:hexanes=2:1). An orange solid was obtained (199 mg, 64% yield based on 3). ESI-MS(−) m/z calcd for [M−H]$^−$ 705.2, found 705.1.

(4'R)-Azido doxorubicin 9,14-cyclic methyl orthoester (6)

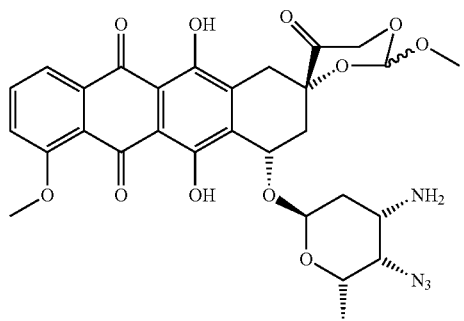

To a stirred solution of 5 (199 mg, 0.28 mmol) in CHCl$_3$ (140 mL) was added NaOH in sat. brine (0.5 M, 14.0 mL). The reaction was stirred vigorously (1200 rpm) at room temperature for 24 h. The completion of the reaction was confirmed by ESI-MS. The organic phase was isolated. The aqueous phase was extracted with CH$_2$Cl$_2$ (50 mL×2). The combined organic phase was washed with brine (50 mL×2) and water (50 mL×2). The organic phase was dried over MgSO$_4$. The solvent was removed under vacuum. The crude product was used in the next step without further purification (80 mg, 47% yield). ESI-MS(−) m/z calcd for [M−H]$^−$ 609.2, found 609.2. ESI-MS(+) m/z calcd for [M+H]$^+$ 611.2, found 611.2.

(4'R)-Dehydroxyamino doxorubicin (DOX-NH$_2$—NH$_2$, 9)

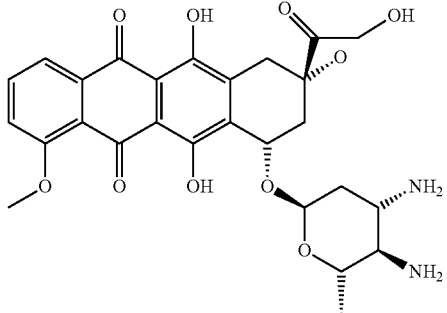

To the crude product 6 (80 mg, 0.13 mmol) in THF (52 mL) was added triphenylphosphine (102 mg, 0.39 mmol) in small portions. The reaction was stirred at room temperature for 48 h. The completion of the reaction was confirmed by ESI-MS. ESI-MS(+) m/z calcd for iminophosphorane (7) [M+H]$^+$ 845.3, found 845.5.

The above reaction was mixed with water (5.2 mL) and stirred at room temperature. The progress of the hydrolysis of iminophosphorane (7) was monitored by ESI-MS, which was complete after 24 h. ESI-MS(+) m/z calcd for (4'R)-dehydroxyamino doxorubicin 9,14-cyclic methyl orthoester (8) [M+H]$^+$ 585.2, found 585.1; and [M+Ph$_3$PO+H]$^+$ 863.3, found 863.3.

To the same reaction mixture, an aliquot of aq. HCl (0.25 M, 1.04 mL, 0.26 mmol) was added. The progress of the reaction was monitored by ESI-MS. The reaction was complete after 24 h. The solvents were removed under vacuum. The reaction mixture was dissolved in MeCN/water (1:1, v/v, 20 mL). The mixture was first suction filtered. The filtrate was then passed through a 0.2 µm PTFE syringe filter. The crude product was purified by preparative HPLC. Preparative HPLC used the (A) water (0.1% v/v CF$_3$CO$_2$H)/(B) CH$_3$CN (0.1% v/v CF$_3$CO$_2$H) solvent system, according to the following protocol: constant flow rate 15.0 mL·min$^{-1}$; 0.0-3.0 min, linear gradient 20-27% B; 3.0-13.0 min, linear gradient 27-37% B; 13.0-15.0 min, linear gradient 37-100% B; 15.0-18.0 min, 100% B; 18.0-20.0 min, linear gradient 100-20% B; 20.0-21.0 min, 20% B. Fractions containing the desired product (T$_R$=11.8 min) were combined and lyophilized to give an orange solid as a bis(trifluoroacetic acid) salt (48 mg, 48% yield based on 6). The purity of 9 was examined by analytical HPLC (T$_R$=17.2 min). Analytical HPLC used the (A) water (0.1% v/v CF$_3$CO$_2$H)/(B) CH$_3$CN (0.1% v/v CF$_3$CO$_2$H) solvent system, according to the following protocol: constant flow rate 1.0 mL·min$^{-1}$; 0.0-5.0 min, 10% B; 5.0-30.0 min, linear gradient 10-100% B; 30.0-33.0 min, 100% B; 33.0-36.0 min, linear gradient 100-10% B; 36.0-40.0 min, 10% B. UV-Vis (50 mM PIPES, 100 mM KCl, pH 7.0) ε$_{490}$=18,300 M$^{-1}$·cm$^{-1}$. The $^1$H NMR spectrum of 9 in DMSO-d$_6$ displayed multiple sets of signals, a feature indicating the presence of multiple species. In contrast, the $^1$H NMR spectrum of 9 in CD$_3$CN/D$_2$O (3:1, v/v) only showed one set of signals. This observation suggested that compound 9 underwent slow conformational interconversions on the NMR timescale in DMSO-d$_6$. $^1$H NMR (400 MHz, CD$_3$CN/D$_2$O 3:1, v/v) δ 7.76-7.64 (m, 2H), 7.41 (d, J=9.0 Hz, 1H), 5.45 (d, J=2.8 Hz, 1H), 4.94 (d, J=2.7 Hz, 1H), 4.69 (d, J=20 Hz, 2H, AB system), 4.16 (dq, J=10.0, 6.3 Hz, 1H), 3.91 (s, 3H), 3.67 (ddd, J=12.0, 10.5, 4.6 Hz, 1H), 3.15 (t, J=10.0 Hz, 1H), 3.00 (d, J=19.2 Hz, 1H, part of an AB system), 2.74 (d, J=18.7 Hz, 1H, part of an AB system), 2.32-2.04 (m, 3H), 1.94 (1H, overlap with CD$_2$HCN), 1.36 (d, J=6.3 Hz, 3H). $^{13}$C{$^1$H} NMR (101 MHz, CD$_3$CN/D$_2$O 3:1, v/v) δ 214.8, 187.7, 187.6, 161.9, 156.7, 155.4, 137.3, 135.6, 134.7 (2), 134.7 (0), 120.8, 120.4, 120.3, 112.2, 112.0, 99.3, 76.7, 70.4, 66.3, 65.5, 57.4, 55.6, 47.6, 36.8, 34.1, 33.2, 17.9. ESI-MS(+) m/z calcd for DOX-NH$_2$—NH$_2$ (9) [M+H]$^+$ 543.2, found 543.4. ESI-MS (−) m/z calcd [M−H]$^-$ 541.2, found 541.2. ESI-HRMS(+) m/z calcd for C$_{27}$H$_{31}$N$_2$O$_{10}$$^+$[M+H]$^+$ 543.1973, found 543.1947.

Doxaliplatin (12)

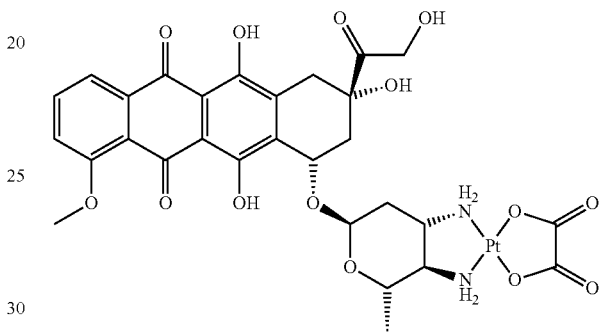

Figure 12:
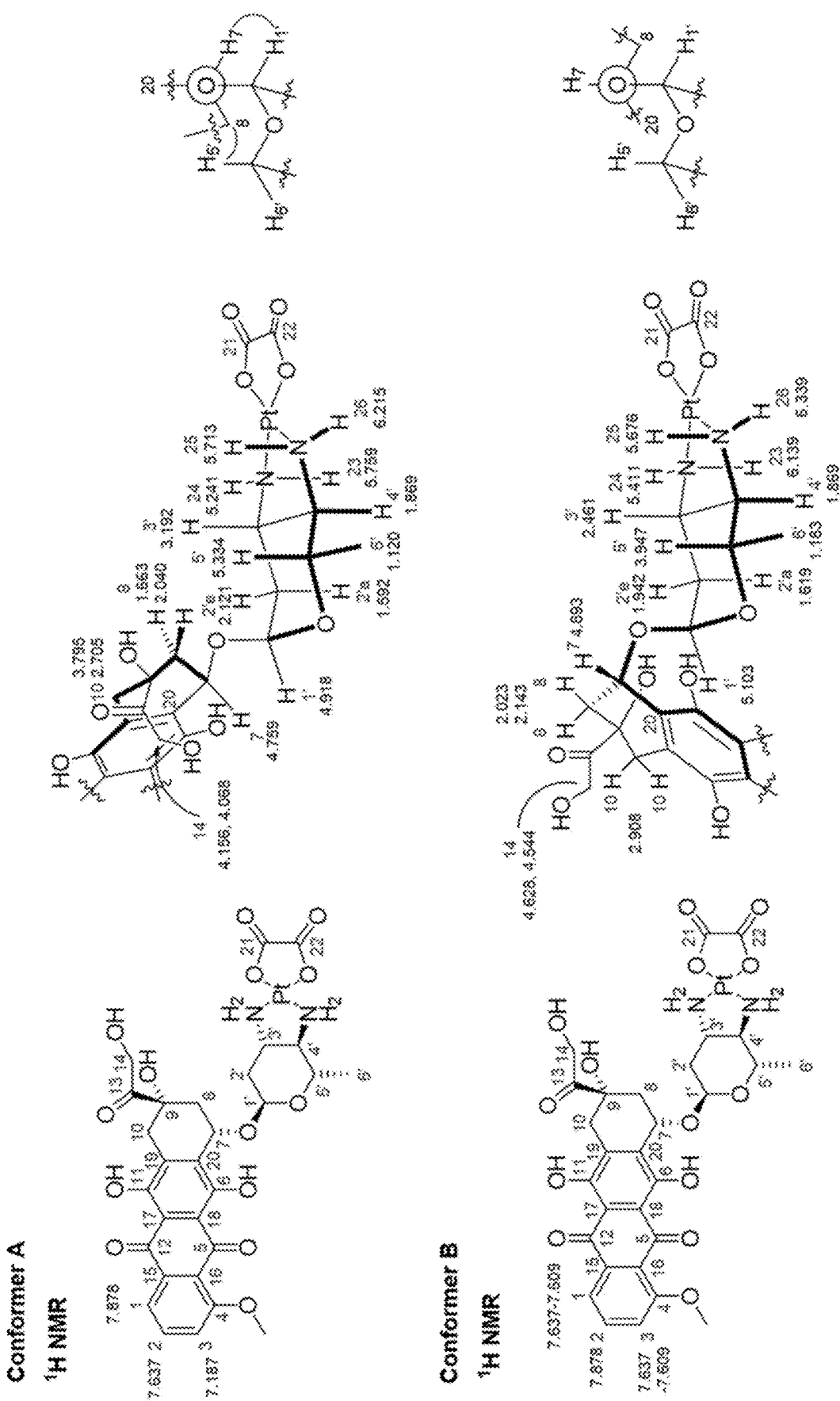
FIG. 12 shows two conformers of doxaliplatin in DMSO-efe detected by NMR spectroscopy.

To a stirred solution of K$_2$PtCl$_4$ (41.5 mg, 0.100 mmol) in water (30 mL), a solution of 9 bis(trifluoroacetic acid) salt (77.0 mg, 0.100 mmol) in water (9 mL) was added in one portion. Red precipitate formed immediately. The reaction was stirred at room temperature for 24 h. To the same solution was added AgNO$_3$ aq. solution (0.10 M, 4.0 mL). The reaction was stirred at room temperature for 24 h. To this mixture was then added K$_2$C$_2$O$_4$ aq. solution (0.20 M, 0.50 mL). The reaction was stirred at room temperature for 24 h. The reaction mixture was lyophilized together with a small amount of C18-reversed phase silica gel. The crude product was first purified using a reverse phase Biotage® SNAP Ultra C18 column (12 g). The purification used the (A) water/(B) MeOH solvent system, according to the following protocol: constant flow rate 12.0 mL·min$^{-1}$; 0.0-3.0 column volume (CV), 0% B; 3.0-10.0 CV, linear gradient 0-80% B; 10.0-20.0 CV, 80% B. Fractions from 13-15 CV were collected and filtered through a 0.2 µm PTFE syringe filter. The combined fractions were further purified by preparative HPLC. Preparative HPLC used the (A) water/(B) MeOH solvent system, according to the following protocol: constant flow rate 15.0 mL·min$^{-1}$; 0.0-3.0 min, linear gradient 25-62% B; 3.0-13.0 min, linear gradient 62-72% B; 13.0-15.0 min, linear gradient 62-100% B; 15.0-17.0 min, 25% B; 17.0-18.0 min, 25% B. Fractions containing the desired product (T$_R$=12.8 min) were combined and lyophilized to give a bright orange solid (24.0 mg, 29% yield based on 9). The purity of 12 was examined by analytical HPLC (T$_R$=25.7 min). Analytical HPLC used the (A) water/(B) MeOH solvent system, according to the following protocol: constant flow rate 1.0 mL·min$^{-1}$; 0.0-5.0 min, 10% B; 5.0-30.0 min, linear gradient 10-100% B; 30.0-33.0 min, 100% B; 33.0-36.0 min, linear gradient 100-10% B; 36.0-40.0 min, 10% B. UV-Vis (water) ε$_{478}$=16,500 M$^{-1}$·cm$^{-1}$. The $^1$H NMR spectrum of 12 in DMF-d$_7$ showed a set of signals with significant line broadening, which indicated that the observed species underwent a slow exchange reaction. The low solubility of 12 in DMF, however, impeded the characterization of the compound. The stability and the relatively high solubility[32] of 12 in DMSO-$d_6$ allowed further characterization of the compound. In contrast to the $^1$H NMR spectrum in DMF-$d_7$, the $^1$H NMR spectrum of 12 in DMSO-$d_6$ revealed two sets of signals, presumably due to the presence of two conformers (FIG. 12). The multiplicity of some $^1$H NMR signals were not determined due to overlap. Conformer A (the population is approximately 45%): $^1$H NMR (500 MHz, DMSO-$d_6$, water suppression using presaturation) δ 7.878 (1H), 7.637 (1H), 7.187 (d, J=7.5 Hz, 1H), 6.215 (br, 1H), 5.759 (br, 1H), 5.713 (br, 1H), 5.334 (m, 1H), 5.241 (m, 1H), 4.918 (br, 1H), 4.759 (1H), 4.156 (d, J=14.6 Hz, 1H, part of an AB system), 4.068 (d, J=14.6 Hz, 1H, part of an AB system), 3.795 (1H), 3.770 (3H), 3.192 (br, 1H), 2.705 (d, J=18.9 Hz, 1H), 2.121 (1H), 2.040 (1H), 1.869 (1H), 1.663 (1H), 1.592 (1H), 1.120 (d, J=5.6 Hz, 3H). Conformer B (the population is approximately 55%): $^1$H NMR (500 MHz, DMSO-$d_6$, water suppression using presaturation) δ 7.878 (1H), 7.637-7.609 (2H), 6.339 (br, 1H), 6.139 (d, J=4.9 Hz, 1H), 5.676 (1H), 5.411 (pseudo t, J=10.3 Hz, 1H), 5.103 (br, 1H), 4.893 (1H), 4.628 (d, J=19.7 Hz, 1H, part of an AB system), 4.544 (d, J=20.0 Hz, 1H, part of an AB system), 3.966 (3H), 3.947 (1H), 2.908 (pseudo t, J=19.2 Hz, 2H), 2.461 (1H), 2.143 (1H), 2.023 (1H), 1.942 (d, J=9.5 Hz, 1H), 1.869 (1H), 1.619 (1H), 1.183 (d, J=6.0 Hz, 3H). Due to the relatively low concentration of 12 in DMSO-7e, only part of the $^{13}$C NMR signals were detected through $^{13}$C-$^1$H correlation experiments. The $^{13}$C NMR signals of Conformer A detected by $^1$H-$^{13}$C HSQC and $^1$H-$^{13}$C HMBC spectroscopy: $^{13}$C{$^1$H} NMR (101 MHz, DMSO-$d_6$) δ 16.98, 31.68, 34.80, 37.89, 55.85, 56.35, 64.07, 65.27, 66.70, 68.15, 98.84, 118.56, 118.86, 134.84, 159.78. The $^{13}$C NMR signals of Conformer B detected by $^1$H-$^{13}$C HSQC and $^1$H-$^{13}$C HMBC spectroscopy: $^{13}$C{$^1$H} NMR (101 MHz, DMSO-$d_6$) δ 17.24, 32.01, 36.73, 37.27, 56.13, 56.31, 63.56, 64.07, 68.53, 69.85, 99.05, 118.68, 118.84, 135.99, 160.62. $^{195}$Pt NMR (86 MHz, DMSO-$d_6$) δ−1989 (br). ESI-MS(+) m/z calcd [M+H]$^+$ 826.1, found 826.2. ESI-HRMS(+) m/z calcd for $C_{29}H_{31}N_2O_{14}Pt^+$[M+H]$^+$ 826.1418, found 826.1419. In the MS/MS experiment, the molecular ion (M+H$^+$) of m/z=826.2 was fragmented to give the following fragments: 736.6, 430.6, 369.0, 340.1, 322.2. Anal. Calcd for $C_{29}H_{30}N_2O_{14}Pt$—$(H_2O)_8$ C, 35.92; H, 4.78; N, 2.89. Found: C, 35.63; H, 4.22; N, 2.77%.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al, describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

Optionally substituted refers to a group which may be substituted or unsubstituted. In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O) (NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$ N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C3-10 carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)

$R^{ff}$, —SH, —SR$^{ee}$, —SSR$^{ee}$, —C(=O)R$^{ee}$, —CO$_2$H, —CO$_2$R$^{ee}$, —OC(=Q)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{1-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(CM alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$ alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal R$^{gg}$ substituents can be joined to form =O or =S; wherein X$^-$ is a counterion.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:
1. A compound of Formula (II):

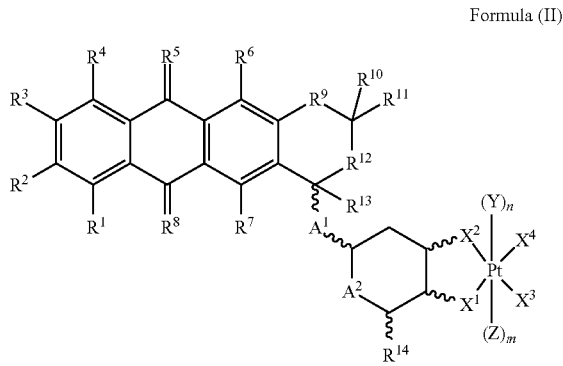

Formula (II)

or a pharmaceutically acceptable salt, solvate, hydrate, polymorph, co-crystal, tautomer, stereoisomer, isotopically labeled derivative, or prodrug thereof;

wherein $R^1$, $R^2$, $R^3$, $R^4$, $R^6$, and $R^7$ are each independently selected from the group consisting of hydrogen, alkyl, aryl, halogen, oxygen, hydroxy, alkoxy, aryloxy, siloxy, amino, alkylamino, arylamino, dialkylamino, diarylamino, imine, alkylimine, arylimine, and —OM;

wherein M is a cation;

wherein $R^5$ and $R^8$ are each independently selected from the group consisting of hydrogen, alkyl, aryl, halogen, oxygen, hydroxy, alkoxy, aryloxy, siloxy, amino, alkylamino, arylamino, dialkylamino, diarylamino, imine, alkylimine, arylimine, and —OM;

wherein $R^9$ and $R^{12}$ are each independently selected from the group consisting of —CR(R')—, carbonyl, imine, alkylimine, and arylimine;

wherein R and R' are independently selected from the group consisting of hydrogen, alkyl, aryl, halogen, hydroxy, alkoxy, aryloxy, siloxy, amino, alkylamino, arylamino, dialkylamino, and diarylamino;

wherein $R^{10}$ and $R^{11}$ are each independently selected from the group consisting of hydrogen, halogen, hydroxy, alkoxy, aryloxy, siloxy, amino, alkylamino, arylamino, dialkylamino, diarylamino, —(C=O)—(CH$_2$)$_k$R$^{15}$, —(CHOR$^{16}$)—(CH$_2$)$_k$R$^{15}$, —(C=NR$^{16}$)—(CH$_2$)$_k$R$^{15}$, —(CHNHR$^{16}$)—(CH$_2$)$_k$R$^{15}$, and —(CHNR$^{16}_2$)—(CH$_2$)$_k$R$^{15}$;

wherein $R^{15}$ is selected from the group consisting of hydrogen, halogen, hydroxy, alkoxy, aryloxy, and siloxy;

wherein $R^{16}$ is selected from the group consisting of hydrogen, alkyl, aryl, and silyl;

wherein k is 0, 1, 2, or 3;

wherein $R^{13}$ and $R^{14}$ are each independently selected from the group consisting of hydrogen, halogen, alkyl, and aryl;

wherein $A^1$ and $A^2$ are each independently selected from the group consisting of oxygen, sulfur, and —NR$^{17}$—;

wherein $R^{17}$ is selected from the group consisting of hydrogen, alkyl, and aryl;

wherein $X^1$ and $X^2$ are each independently selected from the group consisting of amino, alkylamino, arylamino, dialkylamino, diarylamino, oxygen, hydroxy, alkoxy, aryloxy, siloxy, sulfur, thiol, alkyl sulfide, aryl sulfide, alkyl sulfoxide, aryl sulfoxide, sulfinate, selenium, selenol, alkyl selenide, aryl selenide, alkyl selenoxide, aryl selenoxide, and seleninate;

wherein $X^3$ and $X^4$ are each independently selected from the group consisting of amino, alkylamino, arylamino, dialkylamino, diarylamino, heteroarylene, water, halide, carboxylate, hydroxide, alkoxide, aryloxide, siloxide, dialkyl sulfide, diaryl sulfide, alkyl aryl sulfide, dialkyl sulfoxide, diaryl sulfoxide, alkyl aryl sulfoxide, alkyl sulfinate, aryl sulfinate, alkyl sulfonate, aryl sulfonate, sulfite, sulfate, thiosulfate, dialkyl selenide, diaryl selenide, alkyl aryl selenide, dialkyl selenoxide, diaryl selenoxide, alkyl aryl selenoxide, selenite, and seleninate;

wherein Y and Z are each independently selected from the group consisting of hydroxide, alkoxide, aryloxide, siloxide, and halide;

wherein n is 0 or 1;

wherein m is 0 or 1; and wherein M, Y, Z, $A^1$, $A^2$, $X^1$, $X^2$, $X^3$, $X^4$, R, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and/or $R^{17}$ are each independently optionally substituted.

2. The compound of claim 1, wherein $X^1$ and/or $X^2$ is amino.

3. The compound of claim 1, wherein $R^2$, $R^3$, $R^4$, and/or $R^{13}$ are hydrogen.

4. The compound of claim 1, wherein $R^6$, $R^7$, and/or $R^{10}$ are hydroxy, and $R^9$ and/or $R^{12}$ are methylene.

5. The compound of claim 1, wherein $A^1$, $A^2$, $R^5$ and/or $R^8$ are oxygen, and $R^1$ is alkoxy.

6. The compound of claim 1, wherein $R^{11}$ is —(C=O)—$(CH_2)_k R^{15}$, $R^{15}$ is hydroxyl, and k is 1.

7. The compound of claim 1, wherein n and m are both 0.

8. A method of treating cancer in a subject in need thereof, the method comprising administering to the subject a therapeutically effective amount of the compound of claim 1, or a pharmaceutically acceptable salt, solvate, hydrate, polymorph, co-crystal, tautomer, stereoisomer, isotopically labeled derivative, or prodrug thereof.

9. The method of claim 8, wherein the cancer is selected from the group consisting of ovarian cancer, colorectal cancer, breast cancer, lung cancer, prostate cancer, osteosarcoma, and/or leukemia.

10. The method of claim 8, wherein the subject is a human.

* * * * *